United States Patent
Al-Qahtani

(10) Patent No.: US 10,400,591 B2
(45) Date of Patent: Sep. 3, 2019

(54) SYSTEMS AND METHODS FOR ACOUSTIC TESTING OF LAMINATED ROCK TO DETERMINE TOTAL ORGANIC CARBON CONTENT

(71) Applicant: Saudi Arabian Oil Company, Dhahran (SA)

(72) Inventor: Adel Ali Al-Qahtani, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 425 days.

(21) Appl. No.: 15/163,320

(22) Filed: May 24, 2016

(65) Prior Publication Data

US 2017/0342827 A1    Nov. 30, 2017

(51) Int. Cl.
  *E21B 49/00*    (2006.01)
  *E21B 49/02*    (2006.01)
  (Continued)

(52) U.S. Cl.
  CPC ............ *E21B 49/006* (2013.01); *E21B 49/02* (2013.01); *E21B 49/088* (2013.01);
  (Continued)

(58) Field of Classification Search
  CPC ...... G01V 99/005; G01V 11/00; E21B 49/02; E21B 49/088; G06F 17/5009; F16D 3/10;
  (Continued)

(56) References Cited

U.S. PATENT DOCUMENTS

| 3,368,196 A | 2/1968 | Mazzagatti et al. |
| 3,590,228 A | 6/1971 | Burke |

(Continued)

FOREIGN PATENT DOCUMENTS

| WO | 2004031805 A1 | 4/2004 |
| WO | 2011112294 A1 | 9/2011 |

(Continued)

OTHER PUBLICATIONS

Altowairqi "Measuring Ultrasonic Characterization to determine the impact of TOC and the stress field on shale GAS anisotropy" APPEA Journal, p. 245-249, 2013.*

(Continued)

*Primary Examiner* — Regis J Betsch
*Assistant Examiner* — Kaleria Knox
(74) *Attorney, Agent, or Firm* — Bracewell LLP; Constance G. Rhebergen; Christopher L. Drymalla

(57) ABSTRACT

Provided in some embodiments are systems and methods for preparing oriented samples of a laminated rock having different lamination orientations, for each of different stress-levels, transmitting an acoustic pulse through each oriented sample while tri-axially compressing the oriented sample at the stress-level to generate test data indicative of acoustic velocities through the laminated rock at different combinations of lamination orientations and stress levels, determining acoustic velocities through the laminated rock at the different combinations of lamination orientations and stress levels based on the test data, generating a rock model for the laminated rock based on the acoustic velocities, and determining a property of a second laminated rock (e.g., total organic carbon (TOC) content) based on the rock model for the laminated rock.

32 Claims, 7 Drawing Sheets

(51) Int. Cl.

| | |
|---|---|
| *G01N 29/04* | (2006.01) |
| *G01N 29/07* | (2006.01) |
| *G01N 29/22* | (2006.01) |
| *G01N 29/44* | (2006.01) |
| *G01N 33/24* | (2006.01) |
| *E21B 49/08* | (2006.01) |

(52) U.S. Cl.
CPC .......... *G01N 29/043* (2013.01); *G01N 29/07* (2013.01); *G01N 29/227* (2013.01); *G01N 29/4418* (2013.01); *G01N 33/241* (2013.01); *G01N 2291/0231* (2013.01); *G01N 2291/0232* (2013.01); *G01N 2291/0289* (2013.01)

(58) Field of Classification Search
CPC .. G01N 28/043; G01N 29/07; G01N 29/4418; G01N 33/241; G01N 2291/0232; G01N 2291/0289
USPC .......................................................... 703/10
See application file for complete search history.

(56) References Cited

U.S. PATENT DOCUMENTS

| | | | |
|---|---|---|---|
| 4,686,364 | A | 8/1987 | Herron |
| 4,722,220 | A | 2/1988 | Herron |
| 4,972,383 | A | 11/1990 | Lailly |
| 5,507,254 | A * | 4/1996 | Melchior ............... F16D 3/10 123/90.17 |
| 6,718,265 | B2 | 4/2004 | Herron et al. |
| 6,968,274 | B2 | 11/2005 | Tutuncu et al. |
| 8,452,538 | B2 | 5/2013 | Klein et al. |
| 8,531,914 | B2 | 9/2013 | Delpart-Jannaud et al. |
| 8,729,903 | B2 | 5/2014 | Smka et al. |
| 8,914,269 | B2 | 12/2014 | Dutta et al. |
| 2011/0108283 | A1 * | 5/2011 | Srnka .................. G01V 11/00 166/369 |
| 2011/0144913 | A1 | 6/2011 | Klein et al. |
| 2012/0095687 | A1 | 4/2012 | LeCompte |
| 2013/0346048 | A1 * | 12/2013 | Crawford ............. G01V 99/005 703/10 |
| 2014/0297186 | A1 | 10/2014 | Suarez-Rivera et al. |
| 2015/0061669 | A1 | 3/2015 | Hakimuddin |
| 2015/0081265 | A1 * | 3/2015 | Kauerauf ............ G06F 17/5009 703/10 |
| 2015/0111716 | A1 | 4/2015 | Hakimuddin |
| 2016/0070014 | A1 | 3/2016 | Khajeh et al. |

FOREIGN PATENT DOCUMENTS

| | | | | |
|---|---|---|---|---|
| WO | WO2016/0060956 | A1 * | 10/2015 | ............. E21B 49/02 |
| WO | 2016060956 | A1 | 4/2016 | |

OTHER PUBLICATIONS

Lev Vernik "Ultrasonic velocity and anisotropy of hydrocarbon source rocks" Geophysics vol. 57, p. 727-735, 1992.*

Altowairqi "Measuring Ultrasonic Characterization to determine the impact of TOC and the stress filed on shale GAS anisotropy", pp. 245-254 (Year: 2013).*

Shale Velocity and Density as Functions of TOC and Thermal Maturity: Upper Devonian Woodford Shale, Permian /basin, Texas* Nichilas B. Harris (Year: 2015).*

Popp "Influence of bedding planes to EDS-evolution and the coupled HM properties of Opalinus Clay". p. 521-522 (Year: 2007).*

Fertl, Walter H. and Chillingar, George V.; "Total Organic Carbon Content Determined From Well Logs" SPE Formation Evaluation, Jun. 1988; pp. 407-419.

Autric, Andre and Said, Patrice Dumesnil; "Resistivity, Radioactivity and Sonic Transit Time Logs to Evaluate the Organic Content of Low Permeability Rocks" The Log Analyst, May-Jun. 1985; pp. 36-45.

Mendelson, J.D. and Toksoz, M.N.; "Source Rock Characterization Using Multivariate Analysis of Log Data" SPWLA Twenty-Sixth Annual Logging Symposium, Jun. 17-20, 1985; pp. 1-21.

Herron, Susan L.; "A Total Organic Carbon Log for Source Rock Evaluation*" The Log Analyst, Nov.-Dec. 1987; pp. 520-527.

Hussain, F.A.; "Source Rock Identification in the State of Kuwait Using Wireline Logs" SPE 15747, Society for Petroleum Engineers, Fifth SPE Middle East Show, Manama, Bahrain, Mar. 7-10, 1987; pp. 477-488.

Passey, Q.R., et al.; "A Practical Model for Organic Richness from Porosity and Resistivity Logs" The American Association of Petroleum Geologists Bulletin, V. 74. No. 12 (Dec. 1990); pp. 1777-1794.

Meyer, B.L. and Nederlof, M.H.; "Identification of Source Rocks on Wireline Logs by Density/Resistivity and Sonic Transit Time/Resistivity Crossplots" The American Association of Petroleum Geologists Bulletin, V. 68, No. 2 (Feb. 1984); pp. 121-129.

Altowairqi, Y. et al. "Measuring ultrasonic characterisation to determine the impact of TOC and the stress field on shale gas anisotropy." The APPEA Journal 53.1 (2013): 245-254.

Popp, T. et al. "Influence of bedding planes to EDZ-evolution and the coupled HM properties of Opalinus Clay." Physics and Chemistry of the Earth, Parts A/B/C 33 (2008): S374-S387.

Thomsen, L. "Weak elastic anisotropy." Geophysics 51.10 (1986): 1954-1966.

Vernik, L. et al. "Rock physics of organic shales." The Leading Edge 30.3 (2011): 318-323.

Vernik, L. et al. "Ultrasonic velocity and anisotropy of hydrocarbon source rocks." Geophysics 57.5 (1992): 727-735.

International Search Report and Written Opinion for International Application No. PCT/US2017/033454; International Filing Date May 19, 2017; Report dated Aug. 7, 2017; (pp. 1-17).

* cited by examiner

SYSTEMS AND METHODS FOR ACOUSTIC TESTING OF LAMINATED ROCK TO DETERMINE TOTAL ORGANIC CARBON CONTENT

FIELD OF INVENTION

The present invention relates generally to assessment of laminated rock and more particularly to systems and methods for acoustic testing of laminated rock to determine properties of the laminated rock, such as total organic carbon (TOC) content of the laminated rock.

BACKGROUND OF THE INVENTION

Petroleum exploration and production typically emphasizes maximizing reservoir production in a safe and efficient manner. This can include employing enhanced oil recovery (EOR) techniques, such as thermal injection, gas injection and chemical injection, to assist in extracting hydrocarbons from oil and gas reservoirs. These and other techniques for maximizing reservoir production in a safe and efficient manner typical rely on accurate assessments of reservoir properties to determine its potential for petroleum production, as well as the appropriate techniques for maximizing petroleum production petroleum from the reservoir. Total organic carbon (TOC) content, for example, is indicative of a rock's ability to produce hydrocarbons and, thus, can be indicative of a reservoir's potential for petroleum production. Unfortunately, TOC and other reservoir properties can be difficult to ascertain. For example, TOC may be measured by combusting pulverizing samples of rock to generate quantities of carbon monoxide or carbon dioxide that are indicative of the TOC in the sample. Although such a combustion based technique may provide a direct estimation of TOC in rock samples extracted from a reservoir, it may not be able to provide estimation of TOC, or other reservoir properties, in-situ. That is, for example, to determine reservoir properties such as TOC at different depths in a wellbore, a well operator may have extract core samples at the different depths, and subject the samples to the combustion technique or another form of direct assessment to determine the TOC content or other reservoir properties.

SUMMARY OF THE INVENTION

Applicants have recognized that existing techniques for assessing reservoir properties. such as the combustion based techniques for estimating TOC content of a rock sample, can be time consuming and costly. Further, Applicants have recognized the need for reservoir assessment techniques that can provide accurate assessments of TOC content and/or other reservoir properties in a timely and cost effective manner. Applicants have recognized that techniques providing for in-situ assessment of rock properties, e.g., based on well logs, can reduce the delays and cost associated with reservoir assessment techniques that traditional rely heavily on core sampling. For example, in the case of TOC content it would be desirable for a well operator to be able to assess TOC content based on well log data in real-time (e.g., within minutes of obtaining well log data), as opposed to having to suspend drilling operations to extract a core sample, and wait hours, days or even weeks, for the core sample to be assessed to determine the TOC content or other properties of the sample.

Recognizing these and other shortcomings of existing techniques, Applicants have developed novel systems and methods for acoustic testing of laminated rock to determine properties of the rock, such as total organic carbon (TOC) content. Embodiments, provide for generation of a rock model that takes into account relationships between acoustic velocity through the rock, net stress on the rock, lamination orientation of the rock, TOC content of the rock, and composition of the rock (e.g., rock composition and fluid composition). In some embodiments, such a rock model can be employed to determine a property of the laminated rock or similar rock based on other known properties. For example, the rock model can be employed to determine a TOC content of laminated rock when values for the acoustic velocity through the rock, the net stress on the rock, the lamination orientation of the rock, and the composition of the rock (e.g., rock composition and fluid composition) are known or determined (e.g., determined based on well log data, a database of rock properties, and/or the like).

Provided in some embodiments is a system for determining properties of laminated rock. The system including: a laminated rock test system including a tri-axial test fixture adapted to: receive oriented samples of a laminated rock having different lamination orientations; and for each of different stress-levels, transmit an acoustic pulse through each of the oriented samples while tri-axially compressing the oriented sample at the stress-level to generate test data indicative of acoustic velocities through the laminated rock at different combinations of lamination orientations and stress levels; and a non-transitory computer readable storage medium including program instructions for determining properties of laminated rock, the program instructions executable by a computer processor to cause: determining acoustic velocities through the laminated rock at the different combinations of lamination orientations and stress levels based on the test data; generating a rock model for the laminated rock based on the acoustic velocities, the rock model; and determining a property of a second laminated rock based on the rock model for the laminated rock.

Provided in some embodiments is method for determining properties of laminated rock. The method including: preparing oriented samples of a laminated rock having different lamination orientations; for each of different stress-levels, transmit an acoustic pulse through each oriented sample while tri-axially compressing the oriented sample at the stress-level to generate test data indicative of acoustic velocities through the laminated rock at different combinations of lamination orientations and stress levels; determining acoustic velocities through the laminated rock at the different combinations of lamination orientations and stress levels based on the test data; generating a rock model for the laminated rock based on the acoustic velocities, the rock model; and determining a property of a second laminated rock based on the rock model for the laminated rock.

Provided in some embodiments is a non-transitory computer readable storage medium including program instructions for determining properties of laminated rock, the program instructions executable by a computer processor to cause: for each of different stress-levels, transmitting an acoustic pulse through each oriented sample of oriented samples of a laminated rock having different lamination orientations, while tri-axially compressing the oriented sample at the stress-level to generate test data indicative of acoustic velocities through the laminated rock at different combinations of lamination orientations and stress levels; determining acoustic velocities through the laminated rock at the different combinations of lamination orientations and stress levels based on the test data; generating a rock model for the laminated rock based on the acoustic velocities, the rock model; and determining a property of a second laminated rock based on the rock model for the laminated rock.

Provided in some embodiments is a system for determining properties of laminated rock The system including: a laminated rock test system adapted to generate acoustic velocity test data for a laminated rock, the generating including: receiving a plurality of oriented samples of the laminated rock, wherein each of the oriented samples includes a lamination orientation that is different from lamination orientations of other samples of the plurality of oriented samples; for each oriented sample of the plurality of oriented samples: for each stress level of a plurality of different stress levels: compress the sample to generate a tri-axial compressive stress on the sample that corresponds to the stress level; transmit a source acoustic pulse through the oriented sample while the oriented sample is subjected to the tri-axial compressive stress, the transmitted pulse being associated with a pulse generation time; and sense a resulting acoustic pulse corresponding to the source acoustic pulse transmitted through the oriented sample while the oriented sample is subjected to the tri-axial compressive stress, the resulting pulse being associated with a pulse receipt time, the acoustic velocity test data including a subset of acoustic velocity data that is indicative of the pulse generation time and the pulse receipt time, and that is associated with the stress level and the lamination orientation of the oriented sample; and a laminated rock assessment module adapted to: for each lamination orientation of the lamination orientations of the plurality of oriented samples: for each stress level of the plurality of different stress levels: determine, based on one or more of the pulse generation times and one or more of the pulse receipt times of the acoustic velocity test data associated with the lamination orientation and the stress level, an acoustic velocity for the lamination orientation and the stress level; determine a stress coefficient based on the acoustic velocities determined, the stress coefficient being indicative of an impact of compressive stress on velocity of an acoustic signal passing through the laminated rock; determine a lamination orientation coefficient based on the acoustic velocities determined, the lamination orientation coefficient being indicative of an impact of lamination orientation on velocity of an acoustic signal passing through the laminated rock; determine a composition coefficient based on the acoustic velocities determined, the composition coefficient being indicative of an impact of total organic carbon (TOC) content, rock composition and fluid composition on velocity of an acoustic signal passing through the laminated rock; generate a rock model for the laminated rock, wherein the rock model includes: a velocity component indicative of an acoustic velocity of an acoustic signal passing through the laminated rock; a stress component including a weighting of net stress by the stress coefficient; a lamination orientation component including a weighting of lamination orientation by the lamination orientation coefficient; and a composition component including a weighting of TOC, rock composition and fluid composition corresponding to the composition coefficient; and determine a TOC content of a second laminated rock based on the rock model for the laminated rock and an acoustic velocity indicative of velocity of an acoustic signal passing through the second laminated rock.

In certain embodiments, the plurality of oriented samples are prepared from a core sample of the laminated rock extracted from a petroleum reservoir.

In some embodiments, the laminated rock test system includes a test fixture including: a piston adapted to exert, on the plurality of oriented samples, longitudinal compressive force corresponding to the stress level; and a radial chamber adapted to contain a pressurized substance adapted to exert, on the plurality of oriented samples, lateral compressive force corresponding to the stress level.

In certain embodiments, the laminated rock assessment module is adapted to: for each lamination orientation, determine a linear expression for the relationship between acoustic velocities and the stress levels for the lamination orientation, the linear expression including a slope and a y-intercept associated with the lamination orientation; determine a first linear expression for the relationship between the lamination orientations and the corresponding slopes determined, the first linear expression including a slopes-slope corresponding to a slope of the first linear expression, and a slopes-intercept corresponding to a y-intercept of the first linear expression; determine a second linear expression for the relationship between the lamination orientations and the corresponding y-intercepts determined, the second linear expression including an intercepts-slope corresponding to the slope of the second linear expression, and an intercepts-intercept corresponding to a y-intercept of the second linear expression; determine the stress coefficient as a value that corresponds to the slopes-intercept; determine the lamination orientation coefficient as a value that corresponds to the intercepts-slope; and determine the composition coefficient as a value that corresponds to the intercepts-intercept.

In some embodiments, the composition component includes a value for TOC content weighted by a TOC content coefficient, a value for rock composition weighted by a rock composition coefficient, and a value for fluid composition weighted by a fluid composition coefficient, and wherein generating a rock model for the laminated rock includes determining a value for each of the TOC content coefficient, the rock composition coefficient and the fluid composition coefficient based on a value of the composition coefficient.

In certain embodiments, the rock model includes the following:

$$V_p = a_0 + a_1\sigma' + a_2\theta,$$

where:

$$a_0 = bTOC + \Sigma c_i Vol_{rock\_comp,i} + \Sigma d_i Vol_{fluid\_comp,i},$$

and where $V_p$ is acoustic velocity, $a_0$ is the composition coefficient, $a_1$ is the stress coefficient, $a_2$ is the lamination orientation coefficient, $\sigma'$ is a net stress, $\theta$ is lamination orientation, $a_0$ is the composition component, $a_1\sigma'$ is the stress component, $a_2\theta$ is the lamination orientation component, $b$ is a TOC content coefficient, TOC is a value of total organic carbon content, $c_i$ is a rock composition coefficient, $Vol_{rock\_comp,i}$ is a value of rock composition, $d_i$ is a fluid composition coefficient and $Vol_{fluid\_comp,i}$ is a value of fluid composition.

In some embodiments, determining a property of a second laminated rock based on the rock model for the laminated rock includes conducting a logging operation to generate logging data indicative of one or more properties of the second laminated rock in-situ, the one or more properties including the velocity of an acoustic signal passing through the second laminated rock.

In certain embodiments, the system is adapted to control, based on the TOC content of the second laminated rock determined, a drilling operation or production operation in a reservoir formation in which the second laminated rock is located.

Provided in some embodiments is a method for determining properties of laminated rock. The method including: preparing a plurality of oriented samples of a laminated rock, wherein each of the oriented samples includes a lamination orientation that is different from lamination orientations of other samples of the plurality of oriented samples; generating acoustic velocity test data for the laminated rock, the generating including: for each oriented sample of the plurality of oriented samples: for each stress level of a plurality of different stress levels: compressing the sample to generate a tri-axial compressive stress on the sample that corresponds to the stress level; transmitting a source acoustic pulse through the oriented sample while the oriented sample is subjected to the tri-axial compressive stress, the transmitted pulse being associated with a pulse generation time; and sensing a resulting acoustic pulse corresponding to the source acoustic pulse transmitted through the oriented sample while the oriented sample is subjected to the tri-axial compressive stress, the resulting pulse being associated with a pulse receipt time, the acoustic velocity test data including a subset of acoustic velocity data that is indicative of the pulse generation time and the pulse receipt time, and that is associated with the stress level and the lamination orientation of the oriented sample; for each lamination orientation of the lamination orientations of the plurality of oriented samples: for each stress level of the plurality of different stress levels: determining, based on one or more of the pulse generation times and one or more of the pulse receipt times of the acoustic velocity test data associated with the lamination orientation and the stress level, an acoustic velocity for the lamination orientation and the stress level; determining a stress coefficient based on the acoustic velocities determined, the stress coefficient being indicative of an impact of compressive stress on velocity of an acoustic signal passing through the laminated rock; determining a lamination orientation coefficient based on the acoustic velocities determined, the lamination orientation coefficient being indicative of an impact of lamination orientation on velocity of an acoustic signal passing through the laminated rock; determining a composition coefficient based on the acoustic velocities determined, the composition coefficient being indicative of an impact of total organic carbon (TOC) content, rock composition and fluid composition on velocity of an acoustic signal passing through the laminated rock; generating a rock model for the laminated rock, wherein the rock model includes: a velocity component indicative of an acoustic velocity of an acoustic signal passing through the laminated rock; a stress component including a weighting of net stress by the stress coefficient; a lamination orientation component including a weighting of lamination orientation by the lamination orientation coefficient; and a composition component including a weighting of TOC, rock composition and fluid composition corresponding to the composition coefficient; and determining a TOC content of a second laminated rock based on the rock model for the laminated rock and an acoustic velocity indicative of velocity of an acoustic signal passing through the second laminated rock.

In certain embodiments, preparing a plurality of oriented samples of the laminated rock includes dividing a core sample of the laminated rock extracted from a petroleum reservoir into the plurality of oriented samples of the laminated rock.

In some embodiments, compressing the sample to generate a tri-axial compressive stress on the sample that corresponds to the stress level includes: operating a piston of a test fixture to exert, on the plurality of oriented samples, longitudinal compressive force corresponding to the stress level; and pressurizing a substance contained in a radial chamber of the test fixture to exert, on the plurality of oriented samples, lateral compressive force corresponding to the stress level.

In certain embodiments, the method further includes: for each lamination orientation, determining a linear expression for the relationship between acoustic velocities and the stress levels for the lamination orientation, the linear expression including a slope and a y-intercept associated with the lamination orientation; determining a first linear expression for the relationship between the lamination orientations and the corresponding slopes determined, the first linear expression including a slopes-slope corresponding to a slope of the first linear expression, and a slopes-intercept corresponding to a y-intercept of the first linear expression; determining a second linear expression for the relationship between the lamination orientations and the corresponding y-intercepts determined, the second linear expression including an intercepts-slope corresponding to the slope of the second linear expression, and an intercepts-intercept corresponding to a y-intercept of the second linear expression; determining the stress coefficient as a value that corresponds to the slopes-intercept; determining the lamination orientation coefficient as a value that corresponds to the intercepts-slope; and determining the composition coefficient as a value that corresponds to the intercepts-intercept.

In some embodiments, the composition component includes a value for TOC content weighted by a TOC content coefficient, a value for rock composition weighted by a rock composition coefficient, and a value for fluid composition weighted by a fluid composition coefficient, and wherein generating a rock model for the laminated rock includes determining a value for each of the TOC content coefficient, the rock composition coefficient and the fluid composition coefficient based on a value of the composition coefficient.

In certain embodiments, the rock model includes the following:

$$V_p = a_0 + a_1 \sigma' + a_2 \theta,$$

where:

$$a_0 = b\text{TOC} + \Sigma c_i \text{Vol}_{rock\_comp,i} + \Sigma d_i \text{Vol}_{fluid\_comp,i},$$

and where $V_p$ is acoustic velocity, $a_0$ is the composition coefficient, $a_1$ is the stress coefficient, $a_2$ is the lamination orientation coefficient, $\sigma'$ is a net stress, $\theta$ is lamination orientation, $a_0$ is the composition component, $a_1 \sigma'$ is the stress component, $a_2 \theta$ is the lamination orientation component, $b$ is a TOC content coefficient, TOC is a value of total organic carbon content, $c_i$ is a rock composition coefficient, $\text{Vol}_{rock\_comp,i}$ is a value of rock composition, $d_i$ is a fluid composition coefficient and $\text{Vol}_{fluid\_comp,i}$ is a value of fluid composition.

In certain embodiments, determining a property of a second laminated rock based on the rock model for the laminated rock includes: obtaining logging data indicative of one or more properties of the second laminated rock in-situ, the one or more properties including a velocity of an acoustic signal passing through the second laminated rock.

In some embodiments, the method further including controlling, based on the property of the second laminated rock in-situ determined, a drilling operation or production operation in a reservoir formation in which the second laminated rock is located.

Provided in some embodiments is non-transitory computer readable storage medium including program instructions executable by a computer processor to cause the operations of the methods for determining properties of laminated rock described above.

Figure 1:
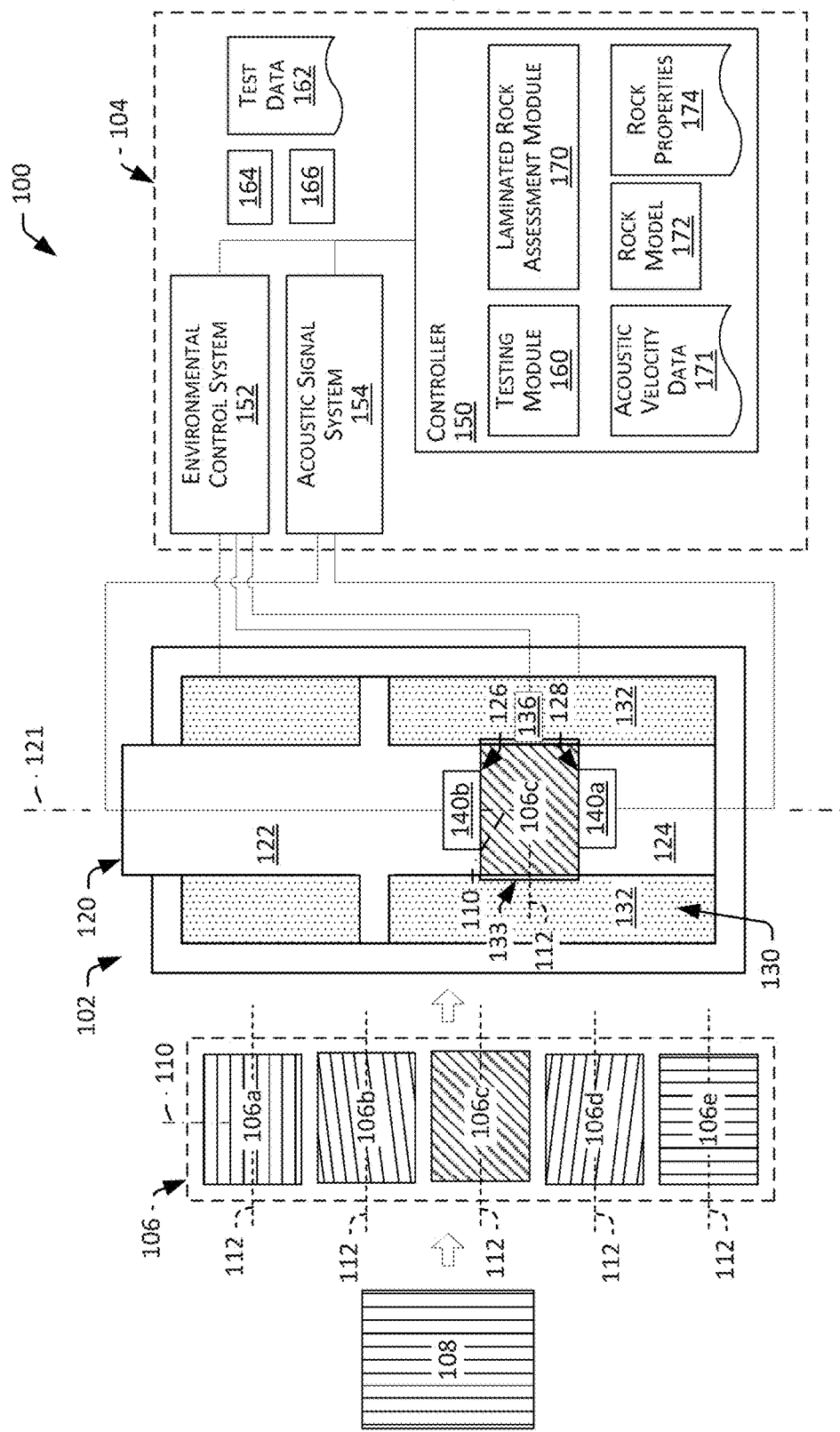
FIG. 1 is a diagram that illustrates a laminated rock assessment environment in accordance with one or more embodiments.

While this disclosure is susceptible to various modifications and alternative forms, specific embodiments thereof are shown by way of example in the drawings and will be described in detail herein. The drawings may not be to scale. It should be understood, however, that the drawings and the detailed descriptions thereto are not intended to limit the disclosure to the particular form disclosed, but, to the contrary, the intention is to cover all modifications, equivalents, and alternatives falling within the spirit and scope of the present disclosure as defined by the appended claims.

DETAILED DESCRIPTION

The present invention will now be described more fully hereinafter with reference to the accompanying drawings in which example embodiments of the invention are shown. This invention may, however, be embodied in many different forms and should not be construed as limited to the illustrated embodiments set forth herein, rather, these example embodiments are provided so that this disclosure will be thorough and complete, and will fully convey the scope of the invention to those skilled in the art.

Described herein are systems and methods for acoustic testing of laminated rock to determine properties of the rock, such as total organic carbon (TOC) content. For example, embodiments provide for generation of a model for rock that takes into account relationships between acoustic velocity through the rock, net stress on the rock, lamination orientation of the rock, TOC content of the rock, as well as composition of the rock (e.g., rock composition and fluid composition). In some embodiments, such a rock model can be employed to determine one or more properties of the laminated rock or similar rock based on other known properties. For example, the rock model can be employed to determine the TOC content of laminated rock when values for the acoustic velocity through the rock, the net stress on the rock, the lamination orientation of the rock, and the composition of the rock (e.g., rock composition and fluid composition) are known or determined (e.g., determined based on well log data, a database of rock properties, and/or the like). As a further example, the rock model can be employed to determine the lamination orientation of the laminated rock when values for the acoustic velocity through the rock, the net stress on the rock, the TOC content of the rock and the composition of the rock (e.g., rock composition and fluid composition) are known or determined (e.g., determined based on well log data, a database of rock properties, and/or the like). As yet another example, the rock model can be employed to determine reservoir pore pressure (e.g., corresponding to the net stress of the rock) when values for the acoustic velocity through the rock, the lamination orientation of the rock, the TOC content of the rock and the composition of the rock (e.g., rock composition and fluid composition) are known or determined (e.g., determined based on well log data, a database of rock properties, and/or the like). In some embodiments, one or more properties of in-situ laminated rock can be determined using, for example, a rock model generated based on acoustic testing of a core sample of laminated rock, and well logs indicative of other properties accounted for in the rock model.

In some embodiments, one or more core samples of laminated rock of a reservoir (e.g., a rock formation known or expected to contain hydrocarbons) is obtained. For example, a well drilling operation may introduce a core drill into a wellbore to obtain (e.g., cut and retrieve) a core sample (e.g., a cylindrical section) of laminated rock (e.g., rock having a sequence of laminations (or "layers") at a given orientation) from the reservoir. In some embodiments, multiple core samples of different lamination orientations are prepared from the one or more core samples of the laminated rock. For example, the core sample of the laminated rock having a given lamination orientation (e.g., 45 degrees) may be divided (e.g., cut or shaped) into multiple oriented core samples that are shaped to have different lamination orientations when disposed in a test fixture (e.g., first, second, third, fourth and fifth oriented samples having lamination orientations of 0°, 25°, 45°, 60°, and 90°, respectively). The test fixture may be designed to tri-axially compress the oriented samples and to obtain acoustic measurements indicative of acoustic velocity through the oriented sample while the sample is subjected to the net compressive stresses resulting from the tri-axial compression applied by the test fixture. Tri-axial compression may refer to simultaneous compression from all directions (x, y, z), providing compressive forces on all faces of the oriented sample simultaneously. In some embodiments, tri-axially compressing an oriented sample may refer to applying compressive forces on all of the faces of the oriented sample, simultaneously. In some embodiments, the tri-axial compression may provide a net stress level on the sample. For example, tri-axial compression on all sides of an oriented sample may result in a net compressive stress of 2000 pounds-per-square-inch (psi) on the oriented sample. In some embodiments, the compressive forces may have a relatively constant distribution of to provide an even compression of the oriented sample from all sides, simultaneously. For example, where an oriented sample is cylindrical in shape, applying tri-axial compression may include applying 2,000 psi of compressive force on the end faces and side faces of the oriented sample, simultaneously, to generate a net tri-axial compressive stress of 2000 psi on the oriented sample. In some embodiments, the compressive forces may have a varying distribution (e.g., larger compressive forces on the ends of the oriented sample and lesser compressive forces on the sides of the oriented sample, or vice versa) to provide varying levels of compression on different portions of the oriented sample, simultaneously. For example, where an oriented sample is cylindrical in shape, applying tri-axial compression may include applying 3,000 psi of compressive force on the end faces of the oriented sample (e.g., longitudinal force) and applying 1,000 psi of compressive force on the side faces of the oriented sample (e.g., lateral force), simultaneously, to generate a net tri-axial compressive stress of 2000 psi on the oriented sample. Thus, evenly and/or unevenly distributed tri-axial compressive forces may generate a net stress of 2000 psi of tri-axial compression on the oriented sample. As discussed herein, tri-axial compression may applied (e.g., during a test procedure) to generate a net stress on the oriented sample that corresponds to a test stress level. Where an oriented sample has a cylindrical shape, the test fixture may include a longitudinally oriented piston that can be operated to apply longitudinal compressive forces on the upper and lower ends of the oriented sample, and include a radial chamber that is designed to surround at least the sides of the oriented sample and that can be filled with a pressurized substance (e.g., a fluid) that exerts compressive forces on the faces of the oriented sample exposed to the pressurized substance. These compressive forces exerted by the pressurized substance can include, for example, the lateral compressive forces acting on the sides of the oriented sample. The longitudinal and/or lateral compressive forces may correspond to a desired test stress level to provide a tri-axial compression that corresponds to the test stress level (e.g., tri-axial compression having relatively constant or varying distribution of forces acting on the faces of the oriented sample that generate a net compressive stress on the oriented sample that correspond to the test stress level). In some embodiments, the tri-axial compression provided by the fixture may correspond to compressive forces laminated rock exposed to when located in a reservoir. Different level of tri-axial compression (e.g., different stress-levels) may be applied to a rock sample to mimic different in-situ stress conditions.

In some embodiments, the pressurized substance may be temperature controlled. A combination of temperature and pressure control can be used to mimic formation environmental conditions. For example, where the oriented sample is associated with a formation temperature of about 50° C., the pressurized substance may be maintained at a temperature of about 50° C. such that the oriented sample is maintained at or otherwise exposed to a temperature laminated rock exposed is to when located in a reservoir. In some embodiments, the test fixture includes temperature sensors for monitoring the temperature of the pressurized substance and/or the oriented sample. For example the test fixture may include in one or more temperature sensors arranged to be suspended in the substance, to be located on or near the lateral faces of the oriented sample and/or to be disposed internal to the oriented sample, to measure the temperature at, near or in the oriented sample, respectively.

In some embodiments, the test fixture includes acoustic transducers (e.g., dual mode, compressional and shear transducers) that are arranged to be located at opposite ends of the oriented sample when the sample is installed in (and tri-axially compressed by) the test fixture. For example, the test fixture may include a first acoustic transducer (e.g., an acoustic transmitter) located at or near an upper face/end of a lower portion of the piston that is positioned to contact/ support/compress a lower end/face of the oriented sample, and a second acoustic transducer (e.g., an acoustic receiver) located at or near a lower face of an upper portion of the piston that is positioned to contact/support/compress an upper face of the oriented sample. The first acoustic transducer (e.g., the acoustic transmitter) may be activated to transmit a source acoustic pulse that is transmitted longitudinally though the oriented sample (e.g., from a lower end/face of the oriented sample to an upper end/face of the oriented sample), and the second acoustic transducer (e.g. the acoustic receiver) may be activated to receive a resulting acoustic pulse (or "return acoustic pulse") that corresponds to the acoustic pulse that was effectively transmitted longitudinally though the oriented sample. In some embodiments, the transducers may have a center frequency of about 1 Megahertz (MHz).

In some embodiments, the source acoustic pulse is provided by an acoustic pulse generator, and/or the resulting acoustic pulse is sensed by a corresponding acoustic pulse receiver. The acoustic pulse generator and the acoustic pulse receiver may be provided as separate units, or an integrated unit (e.g., an acoustic pulse generator/receiver) that is capable of providing the source acoustic pulse and receiving the resulting acoustic pulse. In some embodiments, generation of the source acoustic pulse and receipt of the resulting acoustic pulse is synchronized. For example, a pulse sync signal may be used to trigger the acoustic pulse generator to generate the source acoustic pulse and/or to trigger the acoustic pulse receiver to record the resulting source acoustic pulse. In some embodiments, the time of the generation of the source acoustic pulse (e.g., the pulse generation time), and/or the time of the receipt of the resulting acoustic pulse (e.g., the pulse receipt time) is determined and recorded for the respective pulses. The pulse generation time may correspond to the time at which the source pulse is transmitted from the first acoustic transducer (e.g., an acoustic transmitter), and the pulse receipt time may correspond to the time at which the resulting pulse is received at the second acoustic transducer (e.g., an acoustic receiver).

In some embodiments, the pulse generation time and the pulse receipt time is included in acoustic velocity test data for the oriented sample. The acoustic velocity test data may include other data relating to the pulse and the test conditions, such an identifier of the sample (e.g., including lamination orientation for the sample), the frequency of the source pulse, an indication of the tri-axial stress (e.g., longitudinal and/or lateral compressive stresses) acting on the oriented sample at the time of the pulse, the temperature of the pressurized substance and/or the oriented sample, and/or the like.

In some embodiments, a delay time for an oriented sample can be determined based on the acoustic velocity test data for the oriented sample. For example, the delay time for a pulse may be the difference between the pulse generation time and the pulse receipt time for the pulse. The delay time may be indicative of the duration of time for the pulse to travel through oriented sample (e.g., the time to travel longitudinally through the oriented sample from the acoustic transmitter to the acoustic receiver). Accordingly, this time may be referred to as the "transit time" for the oriented sample. In some embodiments, the transit time for an oriented sample may be determined based on the delay of a single acoustic pulse or multiple pulses (e.g., a transit time for a single acoustic test pulse, or an average of the transit time for 100 acoustic test pulses).

In some embodiments, an acoustic velocity for an oriented sample is determined based on a travel time for the oriented sample. For example, the acoustic velocity may determine as a travel distance for the oriented sample, divided by the transit time. The travel distance may be, for example, the length of the oriented sample and/or the distance between the acoustic transmitter and the acoustic receiver. Where the oriented sample comprises a cylindrical shape and the acoustic transducers are disposed on opposite ends of the cylinder, the length of the cylinder may be considered the length of the oriented sample. Where the oriented sample, has a given lamination orientation and is compressed at a given stress level and temperature, the acoustic velocity can be associated with the rock type, the lamination orientation, the stress level, and the temperature. For example, the acoustic velocity may be stored in associated with the oriented sample (and/or the rock type of the oriented sample), the lamination orientation of the sample, the stress level, and the temperature.

In some embodiments, the above procedure for determining an acoustic velocity for an oriented sample is repeated for a number of different stress levels (e.g., 2,000 psi, 3,000 psi, 4,000 psi, 5,000 psi, 6,000 psi, 7000 psi, 8,000 psi, 9,000 psi, 10,000 psi, 11,000 psi, 12,000 psi, 13,000 psi and 14,000 psi of tri-axial compression) to identify an acoustic velocity for the oriented sample at each stress level of the different stress levels. For example, an oriented sample may be compressed at a first stress level (e.g., 2,000 psi of tri-axial compression) while held at a first temperature, a first set source acoustic pulses (e.g., including one or more acoustic pulses) may be transmitted through the oriented sample to generate a corresponding first set of resulting acoustic pulses, a first transit time for the sample can be determined based on the differences between the pulse generation times for the first set of source acoustic pulses and the corresponding pulse receipt times for the first set resulting acoustic pulses, and a first acoustic velocity (e.g., for a first combination of stress level and lamination orientation) can be determined based on the first transit time and the travel distance. The oriented sample may be compressed at a second stress level (e.g., 3,000 psi of tri-axial compression) while held at the first temperature, a second set source acoustic pulses may be transmitted through the sample to generate a corresponding second set of resulting acoustic pulses, a second transit time for the sample can be determined based on the differences between pulse generation times for the second set of source acoustic pulses and the corresponding pulse receipt times for the second set resulting acoustic pulses, and a second acoustic velocity (e.g., for a second combination of stress level and lamination orientation) can be determined based on the second transit time and the travel distance. This can be repeated for a variety of different stress levels. The first acoustic velocity may be stored in association with the rock type of the oriented sample, the lamination orientation of the oriented sample, the first stress level of the oriented sample, and/or the first temperature, the second acoustic velocity may be associated with the rock type of the oriented sample, the lamination orientation of the oriented sample, the second stress level of the oriented sample, and/or the first temperature, and so forth.

In some embodiments, the above procedures for determining an acoustic velocity for an oriented sample can be repeated for a number of different oriented samples of a laminated rock of different lamination orientations. For example, a first oriented sample having a first lamination orientation (e.g., 0°) may be placed into the test fixture and subjected to different compressive stress levels (e.g., 2,000 psi, 3,000 psi, 4,000 psi, 5,000 psi, 6,000 psi, 7000 psi, 8,000 psi, 9,000 psi, 10,000 psi, 11,000 psi, 12,000 psi, 13,000 psi and 14,000 psi of tri-axial compression) to generate a subset of acoustic velocity test data for the first oriented sample at each of the respective stress levels, a second oriented sample having a second lamination orientation (e.g., 25°) may be placed into the test fixture and subjected different compressive stress levels (e.g., 2,000 psi, 3,000 psi, 4,000 psi, 5,000 psi, 6,000 psi, 7000 psi, 8,000 psi, 9,000 psi, 10,000 psi, 11,000 psi, 12,000 psi, 13,000 psi and 14,000 psi of tri-axial compression) to generate a second subset of acoustic velocity test data for the second oriented sample at each of the respective stress levels, and so forth for each of the different oriented samples. The subsets of acoustic velocity test data may be used to determine an acoustic velocity for each of the lamination orientation and stress level combinations. For example, for the first oriented sample (e.g., having a first lamination orientation of 0°), a first acoustic velocity ($V_p$) of about 12,000 feet-per-sec (ft/sec) may be determined for a first lamination orientation and stress level combination (e.g., 0° lamination orientation and 2,000 psi of tri-axial compression), a second acoustic velocity of about 12,500 feet-per-sec (ft/sec) may be determined for a second lamination orientation and stress level combination (e.g., 0° lamination orientation and 3,000 psi of tri-axial compression), and so forth for each of the different stress levels to generate a first subset of acoustic velocities associated with the first oriented sample, and its first lamination orientation of 0°. For the second oriented sample (e.g., having a second lamination orientation of 25°), a first acoustic velocity ($V_p$) of about 12,700 feet-per-sec (ft/sec) may be determined for a first lamination orientation and stress level combination (e.g., 25° lamination orientation and 2,000 psi of tri-axial compression), a second acoustic velocity of about 13,000 feet-per-sec (ft/sec) may be determined for a second lamination orientation and stress level combination (e.g., 25° lamination orientation and 3,000 psi of tri-axial compression), and so forth for each of the different stress levels to generate a second subset of acoustic velocities associated with the second oriented sample, and its second lamination orientation of 25°. This can be repeated for each of the different lamination orientation and stress level combinations of the testing to generate an acoustic velocity for each of the different lamination orientation and stress level combinations of the testing.

In some embodiments, the determined acoustic velocities can be used to generate a reservoir model for the laminated rock and/or properties for the laminated rock, such as TOC content. For example, the rock model may include components that take into account relationships between acoustic velocity through the rock, net stress on the rock, lamination orientation of the rock, TOC content of the rock, as well as composition of the rock (e.g., rock composition and fluid composition). The rock model may include, for example, a stress component including a weighting of net stress by the stress coefficient, a lamination orientation component including a weighting of lamination orientation by a lamination orientation coefficient, and a composition component including a weighting of TOC, rock composition and fluid composition corresponding to a composition coefficient. The stress coefficient may be indicative of an impact of compressive stress on velocity of an acoustic signal passing through the laminated rock. The lamination orientation coefficient may be indicative of an impact of lamination orientation on velocity of an acoustic signal passing through the laminated rock. The composition coefficient being indicative of an impact of total organic carbon (TOC), rock composition and fluid composition on velocity of an acoustic signal passing through the laminated rock. The stress coefficient, the lamination orientation coefficient, and/or the composition coefficient may be determined based on the acoustic velocities determined for a core sample of laminated rock.

In some embodiments, such a rock model can be employed to determine a property of laminated rock based on other known properties of the rock. For example, the model can be employed to determine the TOC content of laminated rock that is the same or similar to the laminated rock of the core sample (e.g., rock in-situ in the wellbore from which the core sample was extracted) when values for the acoustic velocity through the rock, the net stress on the rock, the lamination orientation of the rock, and the composition of the rock (e.g., rock composition and fluid composition) are known or determined (e.g., determined based on well log data, a database of rock properties, and/or the like). As a further example, the model can be employed to determine the lamination orientation of rock that is the same or similar to the laminated rock of the core sample when values for the acoustic velocity through the rock, the net stress on the rock, the TOC content of the rock and the composition of the rock (e.g., rock composition and fluid composition) are known or determined (e.g., determined based on well log data, a database of rock properties, and/or the like). As yet another example, the rock model can be employed to determine reservoir pore pressure (e.g., corresponding to the net stress of the rock) of rock that is the same or similar to the laminated rock of the core sample when values for the acoustic velocity through the rock, the lamination orientation of the rock, the TOC content of the rock and the composition of the rock (e.g., rock composition and fluid composition) are known or determined (e.g., determined based on well log data, a database of rock properties, and/or the like). In some embodiments, the rock model generated can be used to determine in-situ rock properties, using, for example, the rock model developed using a core sample of laminated rock, and well logs indicative of other properties of the in-situ rock that are accounted for in the rock model.

Figure 2:
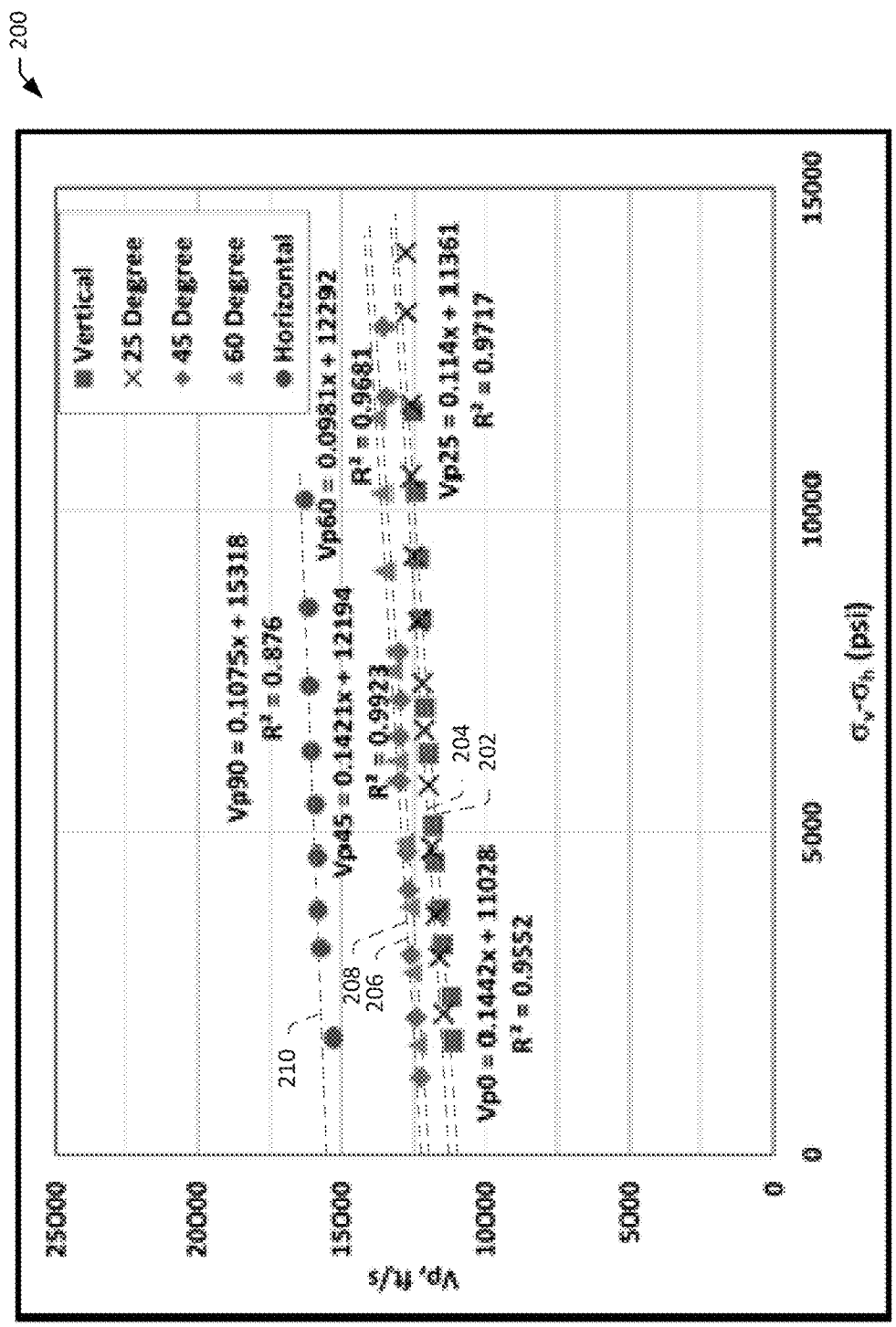
FIG. 2 is a diagram that illustrates a cross-plot of acoustic velocities vs. stress levels for different lamination orientations in accordance with one or more embodiments.

In some embodiments, generation of the rock model includes determining "velocity intercepts" and "slopes" for each of the oriented samples. This can include, for each of the oriented samples, cross-plotting the combinations of the determined acoustic velocities vs. stress levels, generating a fit-line (e.g. via linear regression) for the plot, and determining a y-intercept (or "velocity intercept") for the fit-line and/or a slope for the fit-line. For example, referring to cross plot 200 of FIG. 2, a first velocity intercept of about 11,028 ft/sec (e.g., at a stress level of 0 psi) and a first slope of about 0.1442 may be determined for a first fit-line 202 determined from a first set of cross-plotted points of velocity vs. stress level for the first oriented sample (e.g., having a first lamination orientation of 0°), a second velocity intercept of about 11,361 ft/sec and second slope of about 0.114 may be determined for a second fit-line 204 determined from a second set of cross-plotted points of velocity vs. stress level for the second oriented sample (e.g., having a second lamination orientation of 25°). This can be repeated for each of the different oriented samples and sets of cross-plotted points to determine velocity intercepts and slopes for each of the oriented samples and the associated lamination orientations (e.g., velocity intercepts for each of 0°, 25°, 45°, 60°, and 90° lamination orientations).

In some embodiments, generation of the reservoir model includes determining an a stress coefficient (e.g., indicative of an impact of compressive stress on velocity of an acoustic signal passing through the core sample and similar laminated rock), a lamination orientation coefficient (e.g., indicative of an impact of lamination orientation on velocity of an acoustic signal passing through the core sample and similar laminated rock), a composition coefficient (e.g., indicative of an impact of total organic carbon (TOC), rock composition and fluid composition on velocity of an acoustic signal passing through the core sample and similar laminated rock). The stress coefficient may correspond to the y-intercept of a fit-line for a cross-plot of the slopes determined vs. the lamination orientations. The lamination orientation coefficient and the composition coefficient may correspond to a slope and y-intercept, respectively, of a fit-line for a cross-plot of the velocity intercepts determined vs. the lamination orientations.

Figure 3:
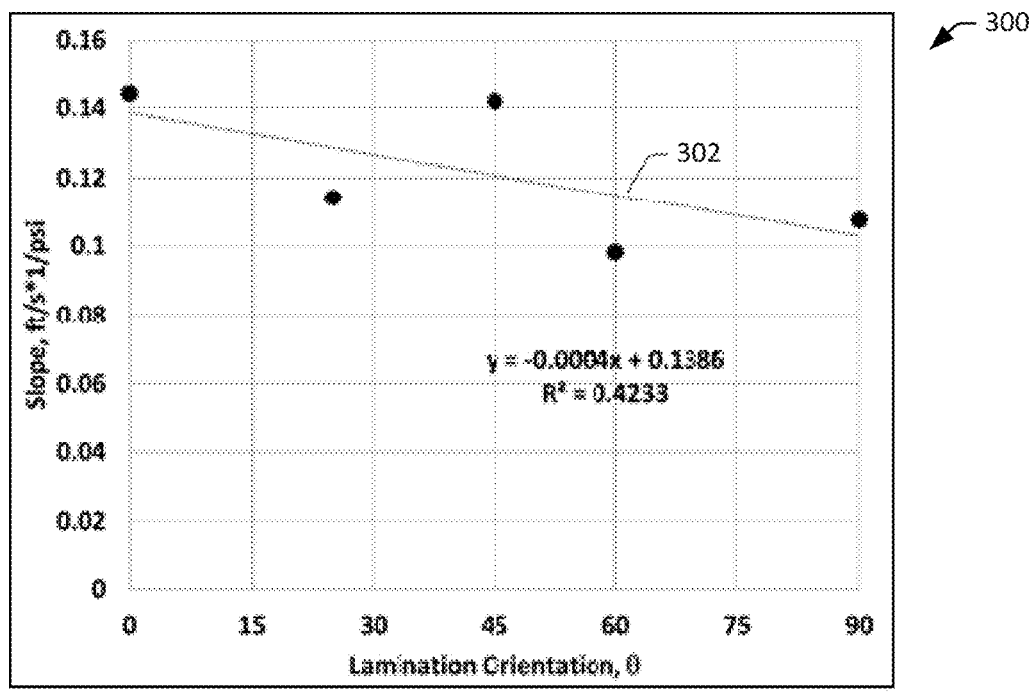
FIG. 3 is a diagram that illustrates a cross-plot of slopes vs. lamination orientations in accordance with one or more embodiments.

In some embodiments, the determination of the stress coefficient includes determining a y-intercept of a fit-line for a cross-plot of the slopes determined vs. the lamination orientations, also referred to herein as the "intercept of the slopes" or the "slopes-intercept". For example, referring to cross plot 300 of FIG. 3, a slopes-intercept of about 0.1386 may be determined for the fit-line 302 determined from a first set of cross-plotted points of the slopes determined vs. the lamination orientations. The stress coefficient may be determined as the value of the slopes-intercept.

Figure 4:
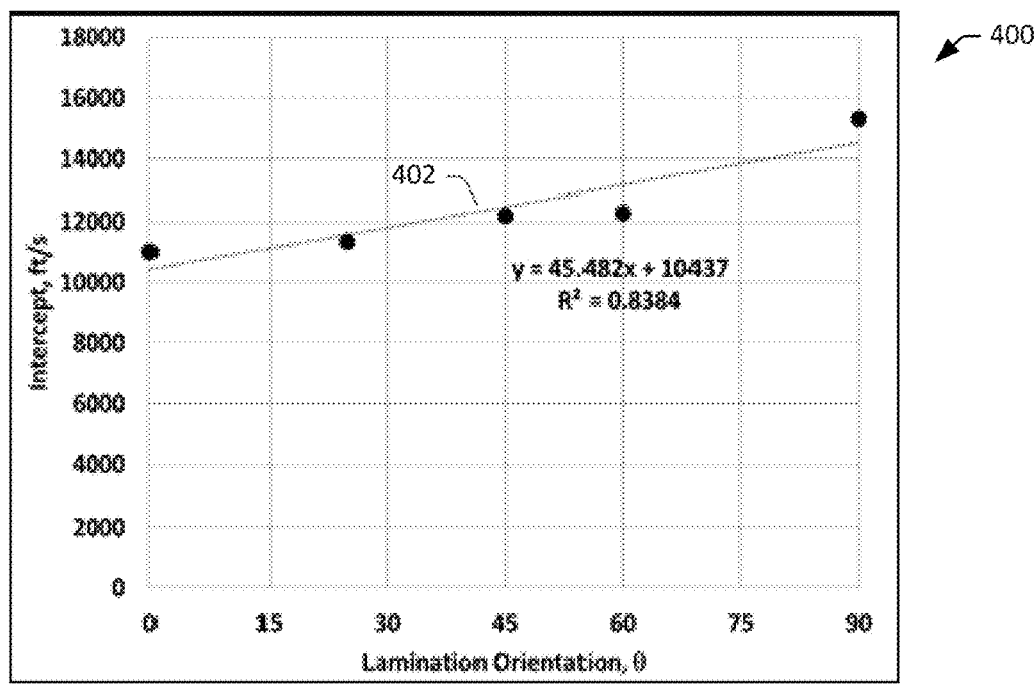
FIG. 4 is a diagram that illustrates a cross-plot of intercepts vs. lamination orientations in accordance with one or more embodiments.

In some embodiments, the determination of the lamination orientation coefficient includes determining a slope of a fit-line for a cross-plot of the intercepts determined vs. the lamination orientations, also referred to herein as the "slope of the intercepts" or the "intercepts-slope". For example, referring to cross plot 400 of FIG. 4, an intercepts-slope of about 45.482 may be determined for a fit-line 402 determined from a first set of cross-plotted points of the intercepts determined vs. the lamination orientations. The lamination orientation coefficient may be determined as the value of the intercepts-slope.

In some embodiments, the determination of the composition coefficient includes determining a y-intercept of a fit-line for a cross-plot of the intercepts determined vs. the lamination orientations, also referred to herein as the "intercept of the intercepts" or the "intercepts-intercept". For example, referring to cross plot 400 of FIG. 4, an intercepts-intercept of about 10,437 may be determined for the fit-line 402 determined from a first set of cross-plotted points of the intercepts determined vs. the lamination orientations. The composition coefficient may be determined as the value of the intercepts-intercept.

In some embodiments, the model can include a combined lamination orientation and stress component that includes a corresponding combined lamination orientation and stress coefficient. The combined lamination orientation and stress component may include a weighting of a product of net stress and lamination orientation by the stress coefficient. In some embodiments, the determination of the combined lamination orientation and stress coefficient includes determining a slope of a fit-line for a cross-plot of the slopes determined vs. the lamination orientations, also referred to herein as the "slope of the slopes" or the "slopes-slope". For example, referring to cross plot 300 FIG. 3, a slopes-slope of about −0.0004 may be determined for the fit-line 302 determined from the first set of cross-plotted points of the slopes determined vs. the lamination orientations. The combined lamination orientation and stress coefficient may be determined as the value of the slopes-slope. As described below, when the combined lamination orientation and stress coefficient is relatively small when compared to the other coefficients, the combined lamination orientation and stress component may have a minimal contribution to the rock model and, in some instances, can be eliminated or otherwise removed from the rock model.

In some embodiments, the model includes an expression of acoustic velocity ($V_p$) as a function of the stress component (e.g., including a weighting of net stress by the stress coefficient), a lamination orientation component (e.g., including a weighting of lamination orientation by a lamination orientation coefficient), a composition component (e.g., including a weighting of TOC, rock composition and fluid composition by a composition coefficient), and a combined lamination orientation and stress component (e.g., including a weighting of a product of net stress and lamination orientation by the combined lamination orientation and stress coefficient). A model may be determined as follows:

$$V_p = a_0 + a_1\sigma' + a_2\theta + a_3\theta\sigma' \tag{1}$$

where $V_p$ is acoustic velocity, $a_0$ is the composition coefficient, $a_1$ is the stress coefficient, $a_2$ is the lamination orientation coefficient, $a_3$ is the combined lamination orientation and stress coefficient, $\sigma'$ is a net stress, and $\theta$ is lamination orientation. The first component ($a_0$) is a composition component, the second component ($a_1\sigma'$) is a stress component, the third component ($a_2\theta$) is a lamination orientation component, and the forth component ($a_3\theta\sigma'$) is a combined lamination orientation and stress component.

As noted above, in some instances, the combined lamination orientation and stress coefficient ($a_3$), and the resulting combined lamination orientation and stress component ($a_3\theta\sigma'$), may be relatively small. For example, substituting the example values for the components discussed above (e.g., $a_0=10,437$, $a_1=0.1386$, $a_2=45.482$, and $a_3=-0.0004$), the model may be determined as follows:

$$V_p = 10,437 + 0.1386\ \sigma' + 45.482\ \theta - 0.0004\ \theta\sigma' \tag{2}$$

In such instances, the combined lamination orientation and stress component ($a_3\theta\sigma'$) may be removed from the expression, or otherwise ignored. That is, combined lamination orientation and stress component ($a_3\theta\sigma'$) may have a minimal impact on the acoustic velocity ($V_p$) and, thus, may not need to be considered in the modeling of the laminated rock. Accordingly, the rock model may be determined as follows:

$$V_p = a_0 + a_1\sigma' + a_2\theta \tag{3}$$

As noted above, the composition component (or coefficient) ($a_0$) may be indicative of TOC content and composition (e.g., rock composition and fluid composition) of the rock modeled. In some embodiments, the composition component/coefficient ($a_0$) may be expressed as follows:

$$a_0 = b\text{TOC} + \Sigma c_i Vol_{rock\_comp,i} + \Sigma d_i Vol_{fluid\_comp,i} \tag{4}$$

where $b$ is a TOC content coefficient, TOC is a value of total organic carbon content, $c_i$ is a rock composition coefficient of rock composition (i), $Vol_{rock\_comp,i}$ is a value for rock composition (e.g., indicative volume of the rock in the sample), $d_i$ is a fluid composition coefficient of fluid composition (i) and $Vol_{fluid\_comp,i}$ is a value for fluid composition (e.g., indicative of volume of the fluid in the sample). The values for rock composition coefficient ($Vol_{rock\_comp,i}$) and/or fluid composition ($Vol_{fluid\_comp,i}$) may be known (e.g., based on documentation and literature for the rock type and/or fluid type generally). For in-situ rock being assed using the model, the values for rock composition coefficient ($Vol_{rock\_comp,i}$) and/or fluid composition ($Vol_{fluid\_comp,i}$) may be determined based on well logs corresponding to the in-situ rock, or published values for the laminated rock.

Values for the coefficients of equation 4, (e.g., b, $c_i$ and $d_i$) may be determined using a numerical solver seeking best-fit values that ensure the summation of TOC component, rock composition component and fluid component is equal or very close to the composition component/coefficient ($a_0$).

Substituting the expression of the composition component/coefficient ($a_0$) of equation 4 for the composition component/coefficient ($a_0$) in equation 3, a model may be determined as follows:

$$V_p = a_1\sigma' + a_2\theta + b\text{TOC} + \Sigma c_i Vol_{rock\_comp,i} + \Sigma d_i Vol_{fluid\_comp,i} \tag{5}$$

Figure 5A:
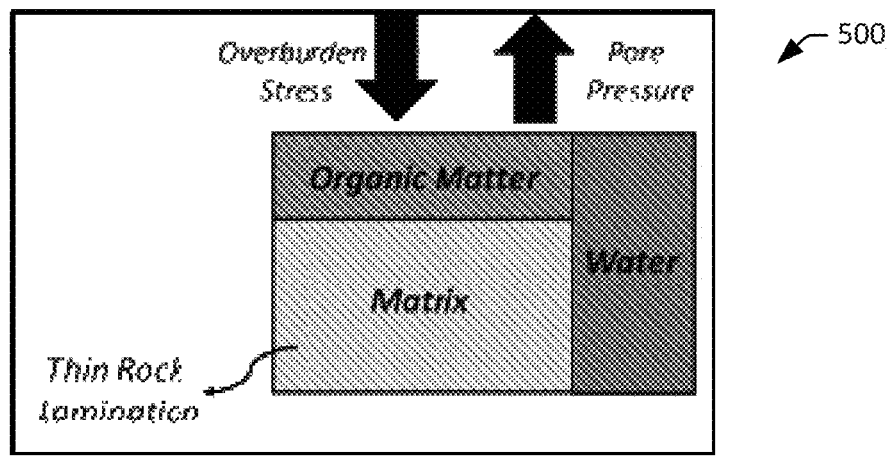
FIG. 5A is a block diagram that illustrates a physical model of immature source rock in accordance with one or more embodiments.
Figure 5B:
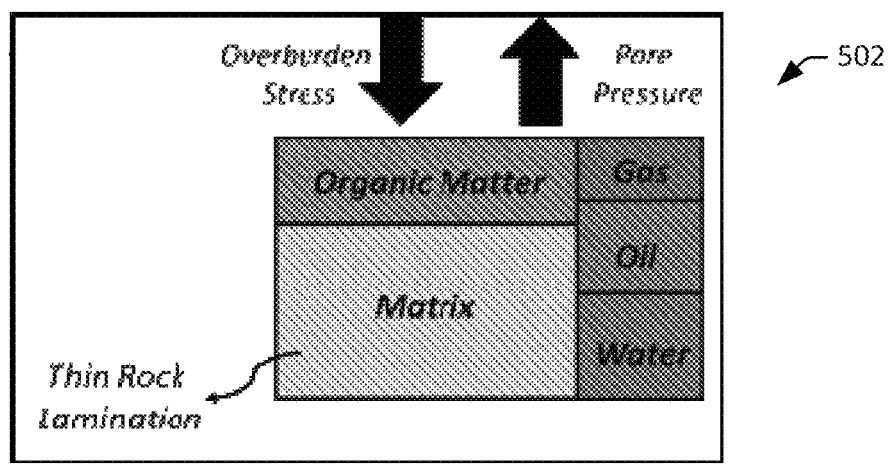
FIG. 5B is a block diagram that illustrates a physical model of mature source rock in accordance with one or more embodiments.

Notably, the model of equation 5 is developed based on a conceptual physical model that includes 5 main components: (1) rock matrix; (2) solid organic matter; (3) fluid(s) filling the pore space of the rock matrix; (4) the net stress (e.g., overburden stress minus pore pressure); and (5) thin rock lamination. The physical model may vary slightly from immature source rock to highly mature source rock due to fluid generated over maturity of the rock. FIG. 5A is a block diagram illustrating a physical model 500 of immature source rock in accordance with one or more embodiments. FIG. 5B is a block diagram illustrating a physical model 502 of mature source rock in accordance with one or more embodiments. Notably, the physical model 502 of mature source rock includes gas and oil components that are absent from the physical model 500 of immature source rock.

FIG. 1 is a diagram that illustrates a laminated rock assessment environment 100 in accordance with one or more embodiments. In some embodiments, the environment 100 includes a test fixture 102 and a test control system 104. The test fixture 102 may provide for acoustic testing of oriented rock samples 106 prepared from a core sample 108 of laminated rock. The oriented core samples 106 may include portions of a single core sample 108 or multiple core samples 106. For example, the core sample 108 may include a cylindrical shaped sample of laminated rock of a reservoir formation, extracted from a wellbore in the formation using a core drill. The core sample 108 may have a given lamination orientation (e.g., 45 degrees). The core sample 108 may be divided (e.g., cut or otherwise shaped) into multiple oriented core samples 106 (e.g., oriented samples 106a-106n) having different lamination orientations. For example, the core sample 108 may be cut into a first sample 106a having a lamination orientation of 0°, a second sample 106b having a lamination orientation of 25°, a third sample 106c having a lamination orientation of 45°, a fourth sample 106d having a lamination orientation of 60°, and a fifth sample 106e having a lamination orientation of 90°. The oriented sample 106 may have a longitudinal axis 110 that, when the oriented sample 106 is positioned in the test fixture 102, is coincident with, or at least parallel to, a liner path extending between an acoustic transmitter and an acoustic receiver of the test fixture 102 that are employed to transmit and receive, respectively, a test acoustic pulse transmitted through the oriented sample 106. Thus, the longitudinal axis 110 may be coincident with, or at least parallel to, a path of travel of a test acoustic pulse (e.g., a transit path) that traverses the oriented sample 106, generated by the acoustic transmitter and received by the acoustic receiver of the test fixture 102. The oriented samples 106 may be shaped such that they have the respective lamination orientations when disposed in the test fixture 102. The lamination orientation of an oriented sample 106 may refer to the direction or general alignment of the layers of the sample relative to a lateral plane 112 of the oriented sample 106. The lateral plane 112 may be perpendicular to the longitudinal axis 110 of the oriented sample 106 and/or the transit path. For example, an oriented sample 106 having a lamination orientation of 0° may have laminations (or "layers") running laterally across the oriented sample 106, generally parallel to the lateral plane 112 of the oriented sample 106 and perpendicular to the longitudinal axis 110 of the oriented sample 106. Such an oriented sample 106 with a lamination orientation of 0° may be said to have a "vertical" orientation. An oriented sample 106 having a lamination orientation of 90° may have laminations running longitudinally along the oriented sample 106, generally perpendicular to lateral plane 112 of the oriented sample 106 and parallel to the longitudinal axis 110 of the oriented sample 106. Such an oriented sample 106 with a lamination orientation of 90° may be said to have a "horizontal" orientation. For example, the first oriented sample 106a (e.g., having a lamination orientation of 0°) may have laminations oriented parallel to the lateral plane 112 of the oriented sample 106a and perpendicular to the longitudinal axis 110 of the oriented sample 106a, as illustrated. When installed in the test fixture 102, the lamination of the first oriented sample 106a may run from a face on one side of the oriented sample 106a to the face on the opposite side of the oriented sample 106a, e.g., running from a left side to right side of the oriented sample 106a in the illustrated orientation of the test fixture 102. The third oriented sample 106c (e.g., having a lamination orientation of 45°) may have laminations oriented at about a 45° angle relative to the lateral plane 112 and the longitudinal axis 110 of the oriented sample 106c, as illustrated. The fifth oriented sample 106e (e.g., having a lamination orientation of 90°) may have laminations oriented perpendicular to the lateral plane 112 of the oriented sample 106e and parallel to the longitudinal axis 110 of the oriented sample 106e, as illustrated. When installed in the test fixture 102, the laminations of the fifth oriented sample 106e may run from a top of the oriented sample 106e at a face 126 of a top piston 122 to a bottom of the sample at a face 128 of a bottom piston 124 of the test fixture 102. Although five oriented samples 106 and lamination orientations are discussed for the purpose of illustration, any suitable number of oriented samples 106 and lamination orientations can be prepared and used.

The test control system 104 may provide for control of the acoustic testing of the oriented rock samples 106, including collecting resulting acoustic velocity test data (also referred to simply as "test data") 162 and/or processing of the test data 162 to generate a rock model 172 for the laminated rock associated with the core sample 108. Such a rock model 172 may be used, for example, to determine properties of the laminated rock or similar rock, such as TOC content, pore pressure, lamination orientation, and/or the like.

The test fixture 102 may be designed to tri-axially compress an oriented sample 106 (e.g., to apply longitudinal and lateral compressive forces on the faces of the oriented sample 106 to provide compression of the oriented sample 106 from all sides) and obtain acoustic measurements indicative of acoustic velocity through the oriented sample 106 while the oriented sample 106 is subjected to the compressive stresses resulting from the tri-axial compression applied by the test fixture 102. The test fixture 102 may include a longitudinally oriented piston 120 that can be operated to apply longitudinal compressive forces on the upper and lower ends of the oriented sample 106. The piston 120 may be arranged to apply a compressive force generally parallel to a longitudinal axis 121 of the piston 120 (e.g., parallel to the transit path, parallel to the longitudinal axis of the oriented sample 106 installed in the test fixture 102 and/or perpendicular to the lateral plane 112 of the oriented sample 106 installed in the test fixture 102). The piston 120 may include an upper piston 122 and a lower piston 124. The piston 120 may be arranged such that when the oriented sample 106 is installed in the test fixture 102 it is disposed between a first/lower face 126 of the upper piston 122 and a second/upper face 128 of the lower piston 124. That is, the oriented sample 106 may be sandwiched between the first/lower face 126 of the upper piston 122 and the second/upper face 128 of the lower piston 124 when the oriented sample 106 is installed in the test fixture 102. The upper face 128 of the lower piston 124 may be positioned to contact/support/compress a lower end/face of the oriented sample 106. The lower face 126 of the upper piston 122 may be positioned to contact/support/compress an upper end/face of the oriented sample 106. FIG. 1 illustrates an example configuration in which the third sample 106c installed in the test fixture 102.

The test fixture 102 may include a radial cavity 130 that is adapted to surround at least the sides of the oriented sample 106 when the oriented sample 106 is installed in the test fixture 102. The radial cavity 130 may be adapted to accept a pressurized substance (e.g., a fluid) 132 that exerts compressive forces on the exterior faces of the oriented sample 106 that are exposed to the pressurized substance 132. In some embodiments some or all of the exterior faces of the oriented sample 106 are covered with a barrier 133 to inhibit interaction between the pressurized substance 132 and the rock and/or fluid of the oriented sample 106. For example, some or all of the rock may be covered in a sleeve (e.g., a rubber sleeve) that inhibits interaction between the pressurized substance 132 and the rock and/or fluid of the oriented sample 106. In such an embodiment, the pressurized substance 132 may act on the exterior of the barrier 133 which may, in-turn, provide corresponding pressure on the adjacent exterior surfaces of the oriented sample 106. In some embodiments, the barrier 133 may be disposed about the lateral faces of the oriented sample 106. For example, where the oriented sample 106 is cylindrical in shape (e.g., with the end being disposed against the faces 126 and 128 of piston 120) the barrier 133 may include a cylindrical sleeve that is disposed about the lateral faces of the oriented sample 106 (e.g., about the curved outer faces of the cylindrical shaped oriented sample 106 that are not covered by the first/lower face 126 of the upper piston 122 and the second/upper face 128 of the lower piston 124 when the oriented sample 106 is installed in the test fixture 102). Such a sleeve may be slid over or wrapped around the oriented sample 106 prior to it being encased in the pressurized fluid 132 (e.g., prior to the pressurized fluid being introduced into the chamber 132). In some embodiments, the barrier 133 may include a coating that is applied on (e.g., painted on) or otherwise disposed the lateral faces. In some embodiments, the compressive forces exerted by the pressurized substance 132 can include, for example, lateral compressive forces acting on the exposed sides of the oriented sample 106 in a direction generally perpendicular to the axis 121. The longitudinal and/or lateral compressive forces may correspond to a test stress level to provide tri-axial compression that corresponds to the test stress level (e.g., longitudinal and lateral forces acting on the faces of the oriented sample 106 that generate a net compressive stress that corresponds to the test stress level). In some embodiments, the tri-axial compression provided by the test fixture 102 may correspond to compressive forces laminated rock 108 is exposed to when located in a reservoir. Different level of tri-axial compression (e.g., different stress-levels) may be applied to oriented sample 106 to mimic different in-situ stress conditions. Although the illustrated embodiment includes a vertically oriented test fixture 102 for the purpose of illustration, embodiments can include any suitable arrangement to provide a tri-axial compression corresponding to a test stress level. For example, the test fixture 102 may be arranged horizontally, with the longitudinal axis 121 being horizontal.

In some embodiments, the pressurized substance 132 may be temperature controlled. A combination of temperature and pressure control can be used to mimic reservoir formation environmental conditions. For example, where the oriented sample 106 is associated with a formation temperature of about 50° C., the pressurized substance 132 may be maintained at a temperature of about 50° C. such that the oriented sample 106 is maintained at or otherwise exposed to a temperature laminated rock is exposed to when located in a reservoir. In some embodiments, the test fixture 102 includes temperature sensors 136 for monitoring the temperature of the pressurized substance 132 and/or the oriented sample 106. For example the test fixture 102 may include in one or more temperature sensors 136 arranged to be suspended in the substance 132, to be located on or near the lateral faces of the oriented sample 106 and/or to be disposed internal to the oriented sample 106, to measure the temperature at, near or in the oriented sample 106, respectively.

In some embodiments, the test fixture 102 includes acoustic transducers 140 (e.g., dual mode, compressional and shear transducers) that are positioned to be located at opposite ends of the oriented sample 106 when the oriented sample 106 is installed in (and tri-axially compressed by) the test fixture 102. For example, the test fixture 102 may include a first acoustic transducer 140a (e.g., an acoustic transmitter) located at or near the upper face 128 of the lower piston 124, and a second acoustic transducer 140b (e.g., an acoustic receiver) located at or near the lower face 126 of the upper piston 122. The first acoustic transducer 140a (e.g., the acoustic transmitter) may be activated to transmit a source acoustic pulse that is transmitted longitudinally though the oriented sample 106 (e.g., coincident or at least parallel with the axis 121, from a lower end/face of the oriented sample 106 to the upper end/face of the oriented sample 106). The second/upper acoustic transducer 140b (e.g. the acoustic receiver) may be activated to receive a resulting acoustic pulse that corresponds to the acoustic pulse that was transmitted longitudinally though the oriented sample 106. That is, the second/upper acoustic transducer 140b (e.g. the acoustic receiver) may receive the acoustic pulse that is transmitted longitudinally though the oriented sample 106. In some embodiments, the transducers 140 (e.g., transducers 140a and/or 140b) may have a center frequency of about 1 MHz. Although embodiments describe an acoustic receiver and transmitter being located at a "top" and "bottom", respectively, of the oriented sample 106a, embodiments can include them in any suitable location. For example, an acoustic receiver and transmitter may be located at a "bottom" and "top", respectively, of the oriented sample 106a. In some embodiments, the acoustic transducers 140 are located long the longitudinal axis 121 such that the acoustic pulse is transmitted through the about center of the oriented sample 106, coincident with the longitudinal axis 121.

In some embodiments, the control system 104 includes a controller 150, an environmental control system 152, and an acoustic signal system 154. The environmental control system 152 may provide for regulating the forces and temperatures the oriented sample 106 is exposed to during acoustic testing of the oriented sample 106. In some embodiments, the environmental control system 152 includes a pressure regulator that regulates the compressive pressure applied to the oriented sample 106 in the test fixture 102 and/or a temperate regulator that regulates the temperature of the pressurized substance 132 and/or the oriented sample 106. For example, the environmental control system 152 may receive an indication of a desired compressive pressure and temperature and, in response, control the pressure regulator to regulate a pressure of hydraulic fluid that causes the piston 120 to compress the oriented sample 106 installed in the test fixture 102 to generate longitudinal compressive force on the oriented sample 106 that corresponds to the desired compressive pressure, regulate the pressure of the pressurized substance 132 in the cavity 130 to generate lateral compressive force on the oriented sample 106 that corresponds to the desired compressive pressure, and/or control the temperature regulator to regulate the temperature of the substance 132 and/or the oriented sample 106 at the desired temperature.

The acoustic pulse system 154 may include an acoustic pulse generator and/or an acoustic pulse receiver. In some embodiments, the acoustic pulse generator provides for generation of the source acoustic pulses and/or the acoustic pulse receiver provides for receipt of the corresponding resulting acoustic pulses. For example, an acoustic pulse generator of the acoustic pulse system 154 may generate a source acoustic pulse that is transmitted into the oriented sample 106 by the first acoustic transducer 140a (e.g., an acoustic transmitter), and/or an acoustic pulse receiver of the acoustic pulse system 154 may sense the resulting acoustic pulse via the second acoustic transducer 140b (e.g., an acoustic receiver). In some embodiments, generation of the source acoustic pulse and receipt of the resulting acoustic pulse is synchronized. For example, a pulse sync signal may be used to trigger the acoustic pulse generator of the acoustic pulse system 154 to generate the source acoustic pulse, and to trigger the acoustic pulse receiver of the acoustic pulse system 154 to record the resulting source acoustic pulse. In some embodiments, the time of the generation of the source acoustic pulse (e.g., the pulse generation time), and/or the time of the receipt of the resulting acoustic pulse (e.g., the pulse receipt time) is determined and recorded for each of the respective pulses. The pulse generation time may correspond to the time at which the source pulse is transmitted from the first acoustic transducer 140a (e.g., an acoustic transmitter), and the pulse receipt time may correspond to the time at which the resulting pulse is received at the second acoustic transducer 140b (e.g., an acoustic receiver).

The controller 150 may provide for control of the testing conditions, as well as collection and processing of associated test data 162. In some embodiments, the controller 150 includes a testing module 160 that provides for control of a tri-axial compression and acoustic pulsing test sequence, and for collection of associated test data 162. For example, the testing module 160 may receive test parameters, such as a series of stress levels (e.g., 2,000 psi, 3,000 psi, 4,000 psi, 5,000 psi, 6,000 psi, 7000 psi, 8,000 psi, 9,000 psi, 10,000 psi, 11,000 psi, 12,000 psi, 13,000 psi and 14,000 psi of tri-axial compression), a test temperature (e.g., 50° C.), a test frequency (e.g., 1 MHz), and an identifier for an oriented sample 106 to be tested (e.g., including lamination orientation, rock type and/or the like for the oriented sample 106). For each of the stress levels of the series of stress levels, the testing module 160 may determine a corresponding compressive pressure, and provide, to the environmental control system 152, an indication of the compressive pressure and the test temperature. The environmental control system 152 may, in response to receiving the indication of the compressive pressure and the test temperature, regulate the pressures of the piston 120 and the pressurized substance 132 (e.g., based on the compressive pressure indicated), resulting in application of a tri-axial compressive force on the oriented sample 106 that corresponds to the stress level, and regulate the temperature of the pressurized substance 132 to maintain the pressurized substance 132 and/or the oriented sample 106 at the test temperature. The environmental control system 152 may provide, to the testing module 160, environmental condition data 164 that is indicative of the current state of the test environment (e.g., pressure and temperature). The testing module 160 may provide, to the acoustic control system 154, an indication of acoustic pulse characteristics, such as the test frequency (e.g., 1 MHz). The acoustic control system 154 may, in response to receipt of the indication of acoustic pulse characteristics, configure itself for generation of one or more acoustic pulses in accordance with the acoustic pulse characteristics. The testing module 160 may monitor the environmental condition data 164 and, in response to determining that the environmental condition data 164 indicates that the test conditions are consentient with the test parameters (e.g., the oriented sample 106 is subjected to a tri-axial compressive stress corresponding to the stress level and the pressurized substance 132 and/or the oriented sample 106 are maintained at the test temperature), the testing module 160 may send a sync pulse to the acoustic signal system 154 to trigger the acoustic signal system 154 to generate a source acoustic pulse and measure a corresponding resulting acoustic pulse. In response to the sync signal, the acoustic signal system 154 may generate one or more source acoustic pulses in accordance with the acoustic pulse characteristics (e.g., having the test frequency of 1 MHz) via the first acoustic transducer 140a (e.g., an acoustic transmitter) and sense corresponding one or more resulting acoustic pulse(s) via the second acoustic transducer 140b (e.g., an acoustic receiver). The acoustic signal system 154 may provide, to the testing module 160, acoustic test data 166 indicative of the pulse generation time and the pulse receipt time for each of the one or more pulses. The environmental condition data 164 and/or the acoustic test data 166 may be collected by the testing module 160, and stored as a subset of test data 162. Thus, the subset of the test data 162 may include acoustic test data 166 that is indicative of an acoustic velocity thought the laminated rock at the stress level and the lamination orientation of the oriented rock sample 106.

Such a testing procedure may be repeated on the oriented sample 106 for each of the different stress levels of the series of stress levels such that the test data 162 includes environmental condition data 164 and acoustic test data 166 for each of the stress levels for the oriented sample 106. For example, the process can be repeated for the first oriented sample 106a at each of the different stress levels (e.g., 2,000 psi, 3,000 psi, 4,000 psi, 5,000 psi, 6,000 psi, 7000 psi, 8,000 psi, 9,000 psi, 10,000 psi, 11,000 psi, 12,000 psi, 13,000 psi and 14,000 psi of tri-axial compression) to generate a subset of test data 162 for the first oriented sample 106a. Thus, the test data 162 may include a subset of test data 162 that is indicative of acoustic velocities through the laminated rock at the different stress levels and the lamination orientation of the oriented sample 106.

The procedure can be repeated for different oriented samples 106 having the same or different lamination orientations to generate test data 162 for a plurality of different lamination orientations for the laminated rock. For example, the procedure can be conducted for the first oriented sample 106a at each of the different stress levels to generate a first subset of test data 162 that is indicative of acoustic velocities thought the laminated rock at the various stress levels and the lamination orientation of the oriented sample 106 (e.g., 0°), the procedure can be conducted for the second oriented sample 106b at each of the different stress levels to generate a second subset of test data 162 that is indicative of acoustic velocities through the laminated rock at the various stress levels and the lamination orientation of the oriented sample 106b (e.g., 25°), and so forth for each of the different oriented sample 106. Accordingly, the above procedures may provide for the generation test data 162 that includes subsets of test data 162 for each of the different combinations of lamination orientations and stress levels. The testing module 162 may store the test data 162, e.g., in a test data database, and/or provide the test data 162 to a laminated rock assessment module 170.

The controller 150 may process the collected test data 160 to determine a corresponding rock model 172 and/or rock properties 174 using the rock model 172. The rock model 172 may take into account the relationships between acoustic velocity through the rock, net stress on the rock, lamination orientation of the rock, TOC content of the rock, as well as composition of the rock (e.g., rock composition and fluid composition). In some embodiments, the rock model 172 can be employed to determine properties of rock, such as TOC content of the laminated rock or similar rock. In some embodiments, the controller 150 includes a laminated rock assessment module ("assessment module") 170.

The assessment module 170 may obtain some or all of the test data 162 (e.g., from testing module 160 or a database where the test data 162 is stored), and determine the rock model 172 based on the test data 162. For example, for each of the combinations of lamination orientation and stress level, the assessment module 170 may (1) determine a corresponding delay time (or "transit time") based on the pair(s) of pulse generation times and pulse receipt times of subset of test data 162 associated with the combination of lamination orientation and stress level, and (2) determine an acoustic velocity for the lamination orientation and stress level based on the delay time determined and the length of the sample, to generate acoustic velocity data 171 indicative of an acoustic velocity for each combination of stress level and lamination orientation. The acoustic velocity data 171 may be associated with the core sample 108. The assessment module 170 may store the acoustic velocity data 171, e.g., in an acoustic velocity database.

The assessment module 170 may determine, for each of the lamination orientations, a linear expression for the relationship between acoustic velocities and the stress levels for the lamination orientation, as well as a slope an y-intercept associated with the liner expression, to generate a slope and y-intercept value for each of the lamination orientations. In some embodiments, this can include, for each of the oriented sample 106, cross-plotting the combinations of the determined acoustic velocities and stress levels, generating a fit-line (e.g. via linear regression) for the plot, and determining a y-intercept (or "velocity intercept") for the fit-line and/or a slope for the fit-line. For example, referring to cross plot 200 FIG. 2, a first velocity intercept of about 11,028 ft/sec (e.g., at a stress level of 0 psi) and a first slope of about 0.1442 may be determined for a first fit-line 202 determined from a first set of cross-plotted points of velocity vs. stress level for the first oriented sample (e.g., having a first lamination orientation of) 0°), a second velocity intercept of about 11,361 ft/sec and second slope of about 0.114 may be determined for a second fit-line 204 determined from a second set of cross-plotted points of velocity vs. stress level for the second oriented sample (e.g., having a second lamination orientation of 25°). This can be repeated for each of the different oriented samples and sets of cross-plotted points to determine corresponding fit-lines 206, 208 and 210 and corresponding velocity intercepts and slopes for each of the oriented samples 106 and the associated lamination orientations (e.g., velocity intercepts for each of 0°, 25°, 45°, 60°, and 90° lamination orientations).

The assessment module 170 may determine a linear expression for the relationship between the slopes and the lamination orientations, as well as a slope an y-intercept associated with the liner expression, to generate a corresponding slope (also referred to herein as the "slope of the slopes" or the "slopes-slope") and y-intercept (the "intercept of the slopes" or the "slopes-intercept") for each of the lamination orientations. For example, referring to cross plot 300 of FIG. 3, a slopes-slope of about −0.0004 and a slope-intercept of about 0.1386 may be determined for the fit-line 302 determined from a first set of cross-plotted points of the slopes determined vs. the lamination orientations.

The assessment module 170 may determine a linear expression for the relationship between the intercepts and the lamination orientations, as well as a slope an y-intercept associated with the liner expression, to generate a corresponding slope (also referred to herein as the "slope of the intercepts" or the "intercepts-slope") and y-intercept (the "intercept of the intercepts" or the "intercepts-intercept") for each of the lamination orientations. For example, referring to cross plot 400 of FIG. 4, an intercepts-slope of about 45.482 and an intercepts-intercept of about 10,437 may be determined for a fit-line 402 determined from a first set of cross-plotted points of the intercepts determined vs. the lamination orientations.

The assessment module 170 may determine the rock model 172 based on the slopes-slope, the slopes-intercept, the intercepts-slope and/or the intercepts-intercept. For example, in accordance with the descriptions of equations 1-5 above, the assessment module 170 may determine a composition component/coefficient ($a_0$) that corresponds to the intercepts-intercept (e.g., $a_0$=10,437), a stress coefficient ($a_1$) that corresponds to the slopes-intercept (e.g., $a_1$=0.1386), a lamination orientation coefficient ($a_2$) that corresponds to the intercepts-slope (e.g., $a_2$=45.482), and a combined lamination orientation and stress coefficient ($a_3$) that corresponds to the slopes-slope (e.g., $a_3$=−0.0004). As discussed above, the contribution of the combined lamination orientation and stress component may be minimal and, thus, the combined lamination orientation and stress component may be eliminated or ignored. In accordance with this, in some embodiments, the assessment module 170 may substitute the determined coefficients into equations 5 and 4, to generate the rock model 172. For example, using the above determined value, the rock model 172 may be expressed as follows:

$$V_p = 0.1386\ \sigma' + 45.482\ \theta + 10{,}437 \quad (6)$$

where:

$$10{,}437 = bTOC + \Sigma c_i Vol_{rock\_comp,i} + \Sigma d_i Vol_{fluid\_comp,i} \quad (7)$$

In some embodiments, the rock model 172 can be employed to determine one or more properties of laminated rock based on other known properties of the rock. For example, the rock model 172 can be employed to determine the TOC content of laminated rock that is the same or similar to the laminated rock used to generate the rock model 172 (e.g., laminated rock similar to core sample 108) when values for the acoustic velocity through the rock, the net stress on the rock, the lamination orientation of the rock, and the rock composition (e.g., rock composition and fluid composition) are known or determined (e.g., determined based on well log data), as illustrated by the following:

$$TOC = \frac{V_p - \left(a_1 \sigma' + a_2 \theta + \sum c_i Vol_{rock_{comp},i} + \sum d_i Vol_{fluid_{comp},i}\right)}{b} \quad (8)$$

As a further example, the rock model 172 can be employed to determine the lamination orientation of laminated rock that is the same or similar to the laminated rock used to generate the rock model 172 (e.g., laminated rock similar to core sample 108) when values for the acoustic velocity through the rock, the net stress on the rock, the TOC content of the rock and the rock composition (e.g., rock composition and fluid composition) are known or determined (e.g., determined based on well log data).

$$\theta = \frac{V_p - \left(a_1 \sigma' + bTOC + \sum c_i Vol_{rock_{comp},i} + \sum d_i Vol_{fluid_{comp},i}\right)}{a_2} \quad (9)$$

As a further example, the model can be employed to determine reservoir pore pressure (e.g., corresponding to the net stress of the rock) when values for the acoustic velocity through the rock, the lamination orientation of the rock, the TOC content of the rock and the rock composition (e.g., rock composition and fluid composition) are known or determined (e.g., determined based on well log data).

$$P_p = \sigma_{ov} \frac{V_p - \left(a_2 \theta + bTOC + \sum c_i Vol_{rock_{comp},i} + \sum d_i Vol_{fluid_{comp},i}\right)}{a_1} \quad (10)$$

where $P_p$ is pore pressure and $\sigma_{ov}$ is overburden stress, and $$\sigma' = \sigma_{ov} - P_p \quad (11)$$

Thus, in some embodiments one or more properties of in-situ laminated rock that is the same or similar to the laminated rock used to generate the rock model 172 (e.g., laminated rock similar to core sample 108) can be determined using the model 172. For example, a well may be logged to generate well log data for the well that is indicative of properties of in-situ rock that is associated with the rock model 172 (e.g., in-situ rock in the formation and/or wellbore from which the core sample 108 was extracted or in-situ rock of a formation and/or wellbore that is similar to the formation and/or wellbore from which the core sample 108 was extracted), the assessment module 170 may use the data from the well logs and/or literature to determine some properties of the rock (e.g., the acoustic velocity through the rock, the net stress on the rock, the lamination orientation of the rock, and the composition of the rock, e.g., rock composition and fluid composition), the assessment module 170 may determine coefficients (e.g., $a_0$, $a_1$, $a_2$, $b$, $c_i$, and $d_i$) for the rock model 172 based on the determined properties, and the assessment module 170 may substitute the determined coefficient into the rock model 172 to determine the property for the rock (e.g., TOC content for the rock, lamination orientation of the rock, or a pore pressure for the rock).

Figure 6:
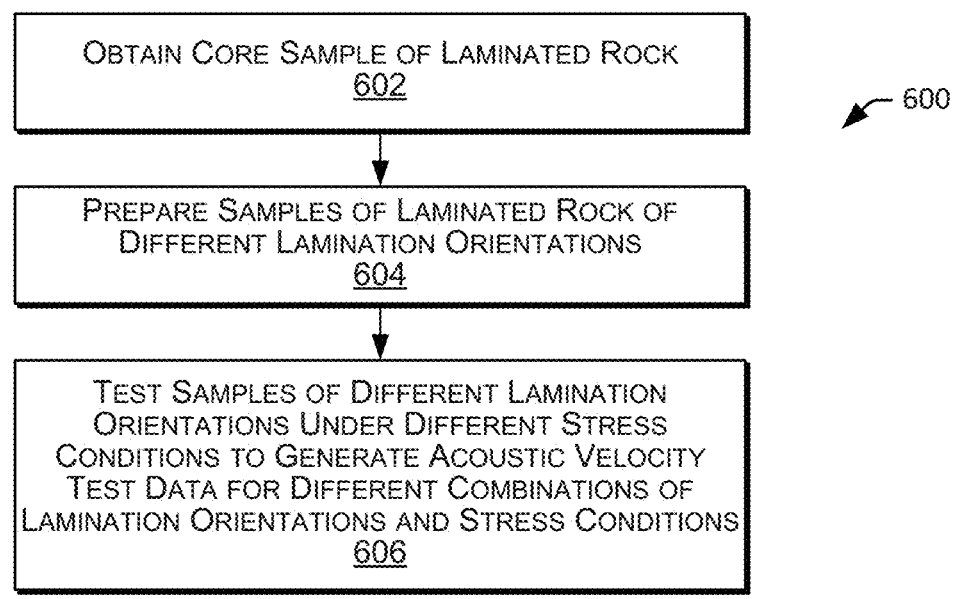
FIG. 6 is a flowchart diagram that illustrates an example method for acoustic testing of laminated rock in accordance with one or more embodiments.

FIG. 6 is a flowchart diagram that illustrates an example method 600 for acoustic testing of rock in accordance with one or more embodiments. The method 600 may include obtaining core samples of laminated rock (block 602). In some embodiments, obtaining core samples of laminated rock may include extracting one or more core samples 108 of laminated rock from a reservoir formation. For example, a core drill may be introduced into a wellbore in a reservoir formation to obtain (e.g., cut and retrieve) a core sample 108 (e.g., a cylindrical section) of laminated rock in the reservoir formation.

The method 600 may include preparing samples of laminated rock of different lamination orientations (block 604). In some embodiments, preparing samples of laminated rock of different orientations includes preparing oriented samples 106 of different lamination orientations from the one or more core samples 108 of the laminated rock. For example, a core sample of the laminated rock having a given lamination orientation (e.g., 45°) may be divided (e.g., cut or shaped) into multiple oriented core samples 106 that are shaped to have different lamination orientations (e.g., first, second, third, fourth and fifth oriented samples 106 having lamination orientations of 0°, 25°, 45°, 60°, and 90°, respectively). The oriented samples 106 may be shaped such that they have the respective lamination orientations when disposed in the test fixture 102. For example, the first oriented sample 106a (e.g., having a lamination orientation of) 0°) may have laminations oriented parallel to the lateral plane 112 of the oriented sample 106a and perpendicular to the longitudinal axis 110 of the oriented sample 106a, as illustrated. When installed in the test fixture 102, the lamination of the first oriented sample 106a may run from a face on one side of the oriented sample 106a to the face on the opposite side of the oriented sample 106a, e.g., running from a left side to right side of the oriented sample 106a in the illustrated orientation of the test fixture 102. The third oriented sample 106c (e.g., having a lamination orientation of 45°) may have laminations oriented at about a 45° angle relative to the lateral plane 112 and the longitudinal axis 110 of the oriented sample 106c, as illustrated. The fifth oriented sample 106e (e.g., having a lamination orientation of 90°) may have laminations oriented perpendicular to the lateral plane 112 of the oriented sample 106e and parallel to the longitudinal axis 110 of the oriented sample 106e, as illustrated. When installed in the test fixture 102, the laminations of the fifth oriented sample 106e may run from a top of the oriented sample 106e at a face 126 of a top piston 122 to a bottom of the sample at a face 128 of a bottom piston 124 of the test fixture 102. Although five oriented samples 106 and lamination orientations are discussed for the purpose of illustration, any suitable number of oriented samples 106 and lamination orientations can be prepared and used.

The method 600 may include testing samples of different lamination orientations under different stress conditions to generate acoustic velocity test data for different combinations of lamination orientations and stress conditions (block 606). In some embodiments, the testing may include, for each, of the oriented samples 106 and a plurality of different compressive stress levels, obtaining measurements indicative of acoustic velocity through the oriented sample 106 while it is subjected to the compressive stress level. For example, each of the oriented samples 106a-106e may be individually inserted into the test fixture 102, and be subjected to tri-axial compression corresponding to each of the different stress levels (e.g., 2,000 psi, 3,000 psi, 4,000 psi, 5,000 psi, 6,000 psi, 7000 psi, 8,000 psi, 9,000 psi, 10,000 psi, 11,000 psi, 12,000 psi, 13,000 psi and 14,000 psi of tri-axial compression) while acoustic measurements are acquired to generate test data 162 that includes subsets of data for each of the different combinations of lamination orientations and stress levels. As described herein, the collected test data 162 may be processed to determine a corresponding rock model 172 and/or rock properties 174 using the rock model 172. Some or all of the testing operations may be controlled by the testing control module 160, as described herein.

Figure 7:
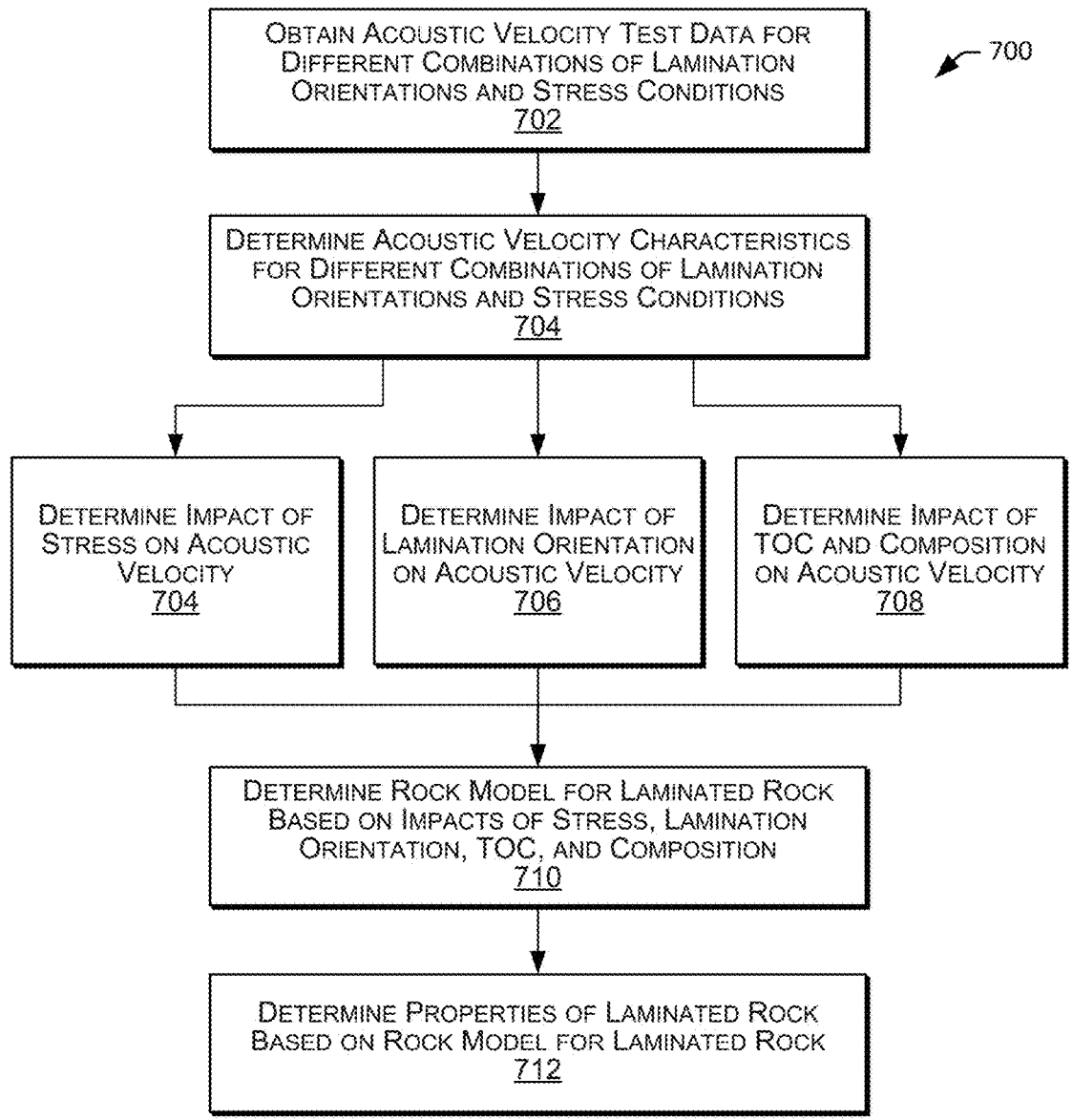
FIG. 7 is a flowchart diagram that illustrates an example method for generating a rock model in accordance with one or more embodiments.

FIG. 7 is a flowchart diagram that illustrates an example method 700 for generating a rock model in accordance with one or more embodiments. In some embodiments, some or all of the operations of method 700 may be performed by the assessment module 170. The method 700 may include obtaining acoustic velocity test data for different combinations of lamination orientations and stress conditions (block 702). In some embodiments, obtaining acoustic velocity test data for different combinations of lamination orientations and stress conditions includes obtaining the collected test data 160. For example, the assessment module 170 may receive the test data 160 from the testing module 160, and/or retrieve it from storage (e.g., from a database).

The method 700 may include determining acoustic velocity characteristics for different combinations of lamination orientations and stress conditions (block 704). In some embodiments, determining acoustic velocity characteristics for different combinations of lamination orientations and stress conditions includes determining an acoustic velocity for each of the different combinations of lamination orientations and stress conditions. For example, for each of the combinations of lamination orientations and stress levels, the assessment module 170 may (1) determine a corresponding delay time based on the pair(s) of pulse generation times and pulse receipt times of subset of test data 162 associated with the combination of lamination orientation and stress level, and (2) determine an acoustic velocity for the lamination orientation and stress level based on the delay time determined and the length of the sample, to generate acoustic velocity data 171 indicative of an acoustic velocity for each combination of stress level and lamination orientation. The acoustic velocity data 171 may be associated with the core sample 108.

The method 700 may include determining an impact of stress, lamination orientation, and TOC and composition (e.g., rock composition and fluid composition) on acoustic velocity (blocks 704, 706 and 708). In some embodiments, determining an impact of stress, lamination orientation and TOC and composition (e.g., rock composition and fluid composition) on acoustic velocity includes determining a composition component/coefficient ($a_0$), a stress coefficient ($a_1$), a lamination orientation coefficient ($a_2$), and/or a combined lamination orientation and stress coefficient ($a_3$) that can be used to generate the rock model 172. The assessment module 170 may determine, for each of the lamination orientations, a linear expression for the relationship between acoustic velocities and the stress levels for the lamination orientation, as well as a slope an y-intercept associated with the liner expression, to generate a slope and y-intercept value for each of the lamination orientations. In some embodiments, this can include, for each of the oriented sample 106, cross-plotting the combinations of the determined acoustic velocities and stress levels, generating a fit-line (e.g. via linear regression) for the plot, and determining a y-intercept (or "velocity intercept") for the fit-line and/or a slope for the fit-line. For example, referring to cross plot 200 of FIG. 2, a first velocity intercept of about 11,028 ft/sec (e.g., at a stress level of 0 psi) and a first slope of about 0.1442 may be determined for a first fit-line 202 determined from a first set of cross-plotted points of velocity vs. stress level for the first oriented sample (e.g., having a first lamination orientation of 0°), a second velocity intercept of about 11,361 ft/sec and second slope of about 0.114 may be determined for a second fit-line 204 determined from a second set of cross-plotted points of velocity vs. stress level for the second oriented sample (e.g., having a second lamination orientation of 25°). This can be repeated for each of the different oriented samples and sets of cross-plotted points to determine corresponding fit-lines 206, 208 and 210, and velocity intercepts and slopes for each of the oriented samples 106 and the associated lamination orientations (e.g., velocity intercepts for each of 0°, 25°, 45°, 60°, and 90° lamination orientations).

The assessment module 170 may determine a linear expression for the relationship between the slopes and the lamination orientations, as well as a slope an y-intercept associated with the liner expression, to generate a corresponding slope (also referred to herein as the "slope of the slopes" or the "slopes-slope") and y-intercept (the "intercept of the slopes" or the "slopes-intercept") for each of the lamination orientations. For example, referring to cross plot 300 of FIG. 3, a slopes-slope of about −0.0004 and a slope-intercept of about 0.1386 may be determined for the fit-line 302 determined from the first set of cross-plotted points of the slopes determined vs. the lamination orientations.

The assessment module 170 may determine a linear expression for the relationship between the intercepts and the lamination orientations, as well as a slope an y-intercept associated with the liner expression, to generate a corresponding slope (also referred to herein as the "slope of the intercepts" or the "intercepts-slope") and y-intercept (the "intercept of the intercepts" or the "intercepts-intercept") for each of the lamination orientations. For example, referring to cross plot 400 of FIG. 4, an intercepts-slope of about 45.482 and an intercepts-intercept of about 10,437 may be determined for the fit-line 402 determined from a first set of cross-plotted points of the intercepts determined vs. the lamination orientations.

In accordance with the descriptions of equations 1-5 above, the assessment module 170 may determine a composition component/coefficient ($a_0$) that corresponds to the intercepts-intercept (e.g., $a_0$=10,437), a stress coefficient ($a_1$) that corresponds to the slope-intercept (e.g., $a_1$=0.1386), a lamination orientation coefficient ($a_2$) that corresponds to the intercepts-slope (e.g., $a_2$=45.482), and a combined lamination orientation and stress coefficient ($a_3$) that corresponds to the slopes-slope (e.g., $a_3$=−0.0004). The composition component/coefficient ($a_0$) may correspond to the impacts of TOC and composition on acoustic velocity, the stress coefficient ($a_1$) may correspond to the impact of stress on acoustic velocity, the lamination orientation coefficient ($a_2$) may correspond to the impact of lamination orientation on acoustic velocity, and the combined lamination orientation and stress coefficient ($a_3$) may correspond to a combined impact of lamination orientation and stress coefficient on acoustic velocity.

The method 700 may include determining a rock model for laminated rock based on impacts of stress, lamination orientation, and TOC and composition (e.g., rock composition and fluid composition) (block 704). In some embodiments, determining a rock model for laminated rock based on impacts of stress, lamination orientation, and TOC and composition includes substituting the coefficients into the modeling of equations 5 and 4. As discussed above, the contribution of the combined lamination orientation and stress component may be minimal and, thus, the combined lamination orientation and stress component may be eliminated or ignored. In accordance with this, in some embodiments, the assessment module 170 may substitute the determined coefficients into equations 5 and 4, to generate the rock model 172, as illustrated above in equations 6 and 7.

The method 700 may include determining properties of laminated rock based on a rock model for laminated rock (block 712). In some embodiments, determining properties of laminated rock based on a rock model for laminated rock includes employing the rock model 172 to determine one or more properties of laminated rock that is the same or similar to the laminated rock used to generate the rock model 172 (e.g., laminated rock similar to core sample 108). For example, the assessment module 170 may employ the rock model 172 to determine TOC content, lamination orientation, pore pressure, and/or the like, as described above with regard to equations 8-11.

In some embodiments, determining properties of laminated rock based on a rock model for laminated rock includes determining one or more properties of in-situ rock using, for example, the model 172 generated from a core sample 108 of laminated rock. For example, a well may be logged to generate well log data for the well that is indicative of properties of in-situ rock that is associated with the rock model 172 (e.g., in-situ rock in the formation and/or wellbore from which the core sample 108 was extracted or in-situ rock of a formation and/or wellbore that is similar to the formation and/or wellbore from which the core sample 108 was extracted), the assessment module 170 may use the data from the well logs and/or literature to determine some properties of the rock (e.g., the acoustic velocity through the rock, the net stress on the rock, the lamination orientation of the rock, and the composition of the rock, e.g., rock composition and fluid composition), the assessment module 170 may determine coefficients (e.g., $a_0$, $a_1$, $a_2$, b, $c_i$, and $d_i$) for the rock model 172 based on the determined properties, and the assessment module 170 may substitute the determined coefficient into the rock model 172 to determine the property for the rock (e.g., TOC content for the rock, lamination orientation of the rock, or a pore pressure for the rock).

Such a rock model 172 can be derived from and incorporated into various drilling and/or production operations. In some embodiments, the rock model 172 can be used to identify the potentiality of hydrocarbon presence in subsurface formations. For example, the rock model 172 can be generated based on a core sample108 that extracted from a wellbore, a logging operation of the wellbore in the formation can be conducted to generate log data that is indicative properties of acoustic velocities through in-situ rock of the wellbore, and the acoustic velocities and other known properties for the rock (e.g., the net stress on the rock, the lamination orientation of the rock, and the composition of the rock, e.g., rock composition and fluid composition) can be substituted into the rock model 172 to determine the TOC content for the in-situ rock, and a potentiality of hydrocarbon presence in the formation can be determined based on the TOC content determined for the in-situ rock using the rock model 172. In some embodiments, the rock model 172 can be used to determine in-situ pore pressure, which can be used to dynamically adjust drilling mud weight and well stability operations. For example, the rock model 172 can be generated based on a core sample 108 that extracted from a wellbore, a logging operation of the wellbore in the formation can be conducted during a drilling operation to generate log data that is indicative properties of acoustic velocities through in-situ rock of the wellbore, and the acoustic velocities and other known properties for the rock (e.g., the net stress on the rock, the lamination orientation of the rock, the TOC content of the rock, and the composition of the rock, e.g., rock composition and fluid composition) can be substituted into the rock model 172 to determine the pore pressure of the in-situ rock, and the drilling operations (e.g., such as drilling mud weight or stability operations) can be adjusted based on the pore pressure determined for the in-situ rock using the rock model 172. In some embodiments, the rock model 172 can be used to determine in-situ lamination orientation (e.g. deviated orientation), which can help in estimating the representative properties of vertical (e.g. Oo) orientated rock.

In some embodiments, the controller 150 can include a computer system (e.g., that is the same or similar to computer system 1000, described below) for performing some or all of the operations described herein, including those described with regard to the controller 150, the testing module 160, the assessment module 170, and/or the methods 600 and/or 700. In some embodiments, the environmental control system 152 can include a computer system (e.g., that is the same or similar to computer system 1000, described below) for performing some or all of the operations described with regard to the environmental control system 152. In some embodiments, the acoustic signal system 154 can include a computer system (e.g., that is the same or similar to computer system 1000, described below) for performing some or all of the operations described with regard to the acoustic signal system 154.

Figure 8:
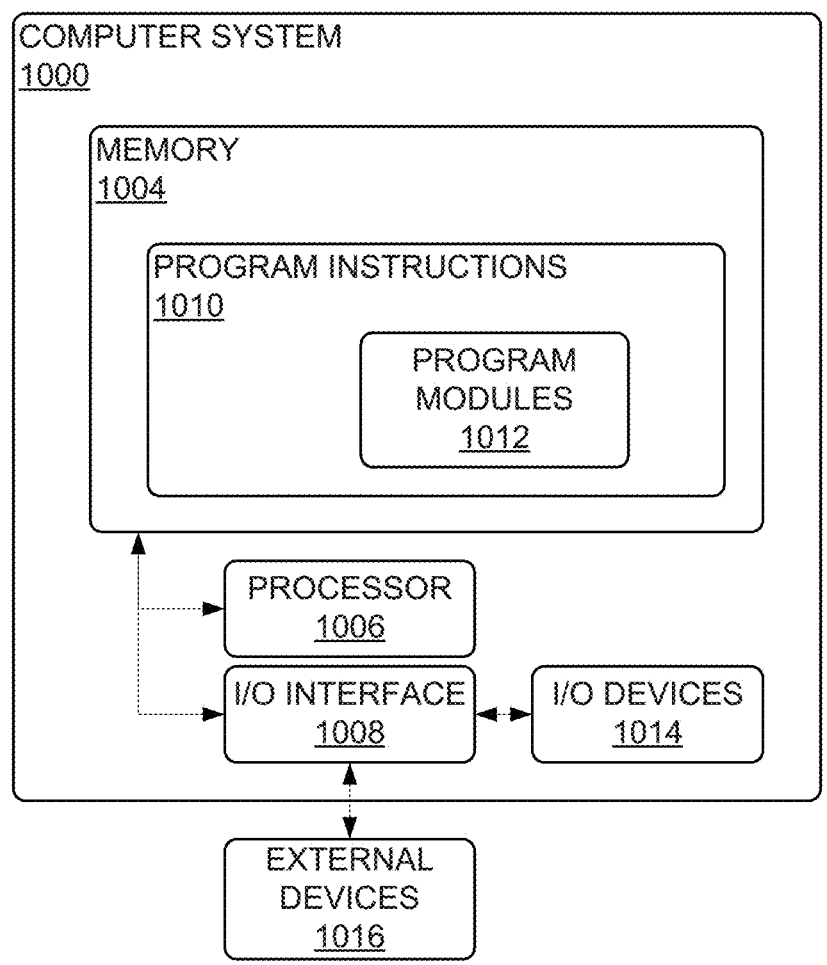
FIG. 8 is a diagram that illustrates an example computer system in accordance with one or more embodiments.

FIG. 8 is a diagram that illustrates an example computer system 1000 in accordance with one or more embodiments. In some embodiments, the computer system 1000 may include a memory 1004, a processor 1006, and an input/output (I/O) interface 1008. The memory 1004 may include non-volatile memory (e.g., flash memory, read-only memory (ROM), programmable read-only memory (PROM), erasable programmable read-only memory (EPROM), electrically erasable programmable read-only memory (EEPROM)), volatile memory (e.g., random access memory (RAM), static random access memory (SRAM), synchronous dynamic RAM (SDRAM)), bulk storage memory (e.g., CD-ROM and/or DVD-ROM, hard drives), and/or the like. The memory 1004 may include a non-transitory computer-readable storage medium having program instructions 1010 stored therein. The program instructions 1010 may include program modules 1012 that are executable by a computer processor (e.g., the processor 1006) to cause the functional operations described herein, including those described with regard to the controller 150, the testing module 160, the assessment module 170, and/or the methods 600 and/or 700. In the context of the controller 150, the program modules 1012 may include the testing module 160, the assessment module 170, and/or one or more modules for performing the operations described with regard to the controller 150, and/or the methods 600 and/or 700. In the context of the environmental control system 152, the program modules 1012 may include one or more modules for performing the operations described with regard to the environmental control system 152. In the context of the acoustic signal system 154, the program modules 1012 may include one or more modules for performing the operations described with regard to the acoustic signal system 154.

The processor 1006 may be any suitable processor capable of executing/performing program instructions. The processor 1006 may include a central processing unit (CPU) that carries out program instructions (e.g., the program instructions of the program module(s) 1012) to perform the arithmetical, logical, and input/output operations described herein. The processor 2006 may include one or more processors. The I/O interface 1008 may provide an interface for communication with one or more I/O devices 1014, such as a joystick, a computer mouse, a keyboard, a display screen (e.g., an electronic display for displaying a graphical user interface (GUI)), and/or the like. The I/O devices 1014 may include one or more of the user input devices. The I/O devices 1014 may be connected to the I/O interface 1008 via a wired or a wireless connection. The I/O interface 1008 may provide an interface for communication with one or more external devices 1016, such as other computers, networks, and/or the like. In some embodiments, the I/O interface 1008 may include an antenna, a transceiver, and/or the like. In some embodiments, the computer system 1000 and/or the external devices 1016 may include one or more pressure gauges, temperature gauges, pumps, and/or the like.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described herein are to be taken as examples of embodiments. Elements and materials may be substituted for those illustrated and described herein, parts and processes may be reversed or omitted, and certain features of the embodiments may be utilized independently, all as would be apparent to one skilled in the art after having the benefit of this description of the embodiments. Changes may be made in the elements described herein without departing from the spirit and scope of the embodiments as described in the following claims. Headings used herein are for organizational purposes only and are not meant to be used to limit the scope of the description.

It will be appreciated that the processes and methods described herein are example embodiments of processes and methods that may be employed in accordance with the techniques described herein. The processes and methods may be modified to facilitate variations of their implementation and use. The order of the processes and methods and the operations provided therein may be changed, and various elements may be added, reordered, combined, omitted, modified, etc. Portions of the processes and methods may be implemented in software, hardware, or a combination thereof. Some or all of the portions of the processes and methods may be implemented by one or more of the processors/modules/applications described herein.

As used throughout this application, the word "may" is used in a permissive sense (i.e., meaning having the potential to), rather than the mandatory sense (i.e., meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the phrase "based on" does not limit the associated operation to being solely based on a particular item. Thus, for example, processing "based on" data A may include processing based at least in part on data A and based at least in part on data B unless the content clearly indicates otherwise. As used throughout this application, the term "from" does not limit the associated operation to being directly from. Thus, for example, receiving an item "from" an entity may include receiving an item directly from the entity or indirectly from the entity (e.g., via an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

What is claimed is:

1. A system for determining properties of laminated rock, comprising:
   a laminated rock test system configured to generate acoustic velocity test data for a laminated rock, the generating comprising:
      receiving a plurality of oriented samples of the laminated rock prepared from a core sample of the laminated rock extracted from a rock formation, wherein each of the oriented samples comprises a lamination orientation that is different from lamination orientations of other samples of the plurality of oriented samples;
      for each oriented sample of the plurality of oriented samples:
         for each stress level of a plurality of different stress levels:
            compress the sample to generate a tri-axial compressive stress on the sample that corresponds to the stress level;
            transmit a source acoustic pulse through the oriented sample while the oriented sample is subjected to the tri-axial compressive stress, the transmitted pulse being associated with a pulse generation time; and
            sense a resulting acoustic pulse corresponding to the source acoustic pulse transmitted through the oriented sample while the oriented sample is subjected to the tri-axial compressive stress, the resulting pulse being associated with a pulse receipt time,
         the acoustic velocity test data comprising a subset of acoustic velocity data that is indicative of the pulse generation time and the pulse receipt time, and that is associated with the stress level and the lamination orientation of the oriented sample; and
   a laminated rock assessment module configured to:
      for each lamination orientation of the lamination orientations of the plurality of oriented samples:
         for each stress level of the plurality of different stress levels:
            determine, based on one or more of the pulse generation times and one or more of the pulse receipt times of the acoustic velocity test data associated with the lamination orientation and the stress level, an acoustic velocity for the lamination orientation and the stress level;
      determine a stress coefficient based on the acoustic velocities determined, the stress coefficient being indicative of an impact of compressive stress on velocity of an acoustic signal passing through the laminated rock;
      determine a lamination orientation coefficient based on the acoustic velocities determined, the lamination orientation coefficient being indicative of an impact of lamination orientation on velocity of an acoustic signal passing through the laminated rock;
      determine a composition coefficient based on the acoustic velocities determined, the composition coefficient being indicative of an impact of total organic carbon (TOC) content, rock composition and fluid composition on velocity of an acoustic signal passing through the laminated rock;
      generate a rock model for the laminated rock, wherein the rock model comprises:
         a velocity component indicative of an acoustic velocity of an acoustic signal passing through the laminated rock;
         a stress component comprising a weighting of net stress by the stress coefficient;
         a lamination orientation component comprising a weighting of lamination orientation by the lamination orientation coefficient; and
         a composition component comprising a weighting of TOC, rock composition and fluid composition corresponding to the composition coefficient,
         the rock model comprising the following:

$$V_p = a_0 + a_1\sigma' + a_2\theta,$$

where:

$$a_0 = b\text{TOC} + \Sigma c_i Vol_{rock\_comp,i} + \Sigma d_i Vol_{fluid\_comp,i},$$

where $V_p$ is acoustic velocity, $a_0$ is the composition coefficient, $a_1$ is the stress coefficient, $a_2$ is the lamination orientation coefficient, $\sigma'$ is a net stress, $\theta$ is lamination orientation, $a_0$ is the composition component, $a_1\sigma'$ is the stress component, $a_2\theta$ is the lamination orientation component, b is a TOC content coefficient, TOC is a value of total organic carbon content, $c_i$ is a rock composition coefficient, $Vol_{rock\_comp,i}$ is a value of rock composition, $d_i$ is a fluid composition coefficient and $Vol_{fluid\_comp,i}$ is a value of fluid composition;
      conduct a logging of a wellbore comprising obtaining logging data indicative of an acoustic velocity of acoustic signals passing through second laminated rock of the wellbore in-situ; and
      determine, based on application of the acoustic velocity of acoustic signals passing through the second laminated rock of the wellbore in-situ to the rock model, a TOC content of the second laminated rock.

2. The system of claim 1, wherein the rock formation comprises a petroleum reservoir.

3. The system of claim 1, wherein the laminated rock test system comprises a test fixture comprising:
   a piston configured to exert, on the plurality of oriented samples, longitudinal compressive force corresponding to the stress level; and
   a radial chamber configured to contain a pressurized substance configured to exert, on the plurality of oriented samples, lateral compressive force corresponding to the stress level.

4. The system of claim 1, wherein the laminated rock assessment module is configured to:
   for each lamination orientation, determine a linear expression for the relationship between acoustic velocities and the stress levels for the lamination orientation, the linear expression comprising a slope and a y-intercept associated with the lamination orientation;

determine a first linear expression for the relationship between the lamination orientations and the corresponding slopes determined, the first linear expression comprising a slopes-slope corresponding to a slope of the first linear expression, and a slopes-intercept corresponding to a y-intercept of the first linear expression;

determine a second linear expression for the relationship between the lamination orientations and the corresponding y-intercepts determined, the second linear expression comprising an intercepts-slope corresponding to the slope of the second linear expression, and an intercepts-intercept corresponding to a y-intercept of the second linear expression;

determine the stress coefficient as a value that corresponds to the slopes-intercept;

determine the lamination orientation coefficient as a value that corresponds to the intercepts-slope; and determine the composition coefficient as a value that corresponds to the intercepts-intercept.

5. The system of claim 1, wherein generating a rock model for the laminated rock comprises determining a value for each of the TOC content coefficient, the rock composition coefficient and the fluid composition coefficient based on a value of the composition coefficient.

6. The system of claim 1, wherein the system is configured to control, based on the TOC content of the second laminated rock determined, a drilling operation or production operation in a reservoir formation in which the second laminated rock is located.

7. A method for determining properties of laminated rock, the method comprising:

preparing a plurality of oriented samples of a laminated rock from a core sample of the laminated rock extracted from a rock formation, wherein each of the oriented samples comprises a lamination orientation that is different from lamination orientations of other samples of the plurality of oriented samples;

generating acoustic velocity test data for the laminated rock, the generating comprising:

for each oriented sample of the plurality of oriented samples:

for each stress level of a plurality of different stress levels:

compressing the sample to generate a tri-axial compressive stress on the sample that corresponds to the stress level;

transmitting a source acoustic pulse through the oriented sample while the oriented sample is subjected to the tri-axial compressive stress, the transmitted pulse being associated with a pulse generation time; and sensing a resulting acoustic pulse corresponding to the source acoustic pulse transmitted through the oriented sample while the oriented sample is subjected to the tri-axial compressive stress, the resulting pulse being associated with a pulse receipt time, the acoustic velocity test data comprising a subset of acoustic velocity data that is indicative of the pulse generation time and the pulse receipt time, and that is associated with the stress level and the lamination orientation of the oriented sample;

for each lamination orientation of the lamination orientations of the plurality of oriented samples:

for each stress level of the plurality of different stress levels:

determining, based on one or more of the pulse generation times and one or more of the pulse receipt times of the acoustic velocity test data associated with the lamination orientation and the stress level, an acoustic velocity for the lamination orientation and the stress level;

determining a stress coefficient based on the acoustic velocities determined, the stress coefficient being indicative of an impact of compressive stress on velocity of an acoustic signal passing through the laminated rock;

determining a lamination orientation coefficient based on the acoustic velocities determined, the lamination orientation coefficient being indicative of an impact of lamination orientation on velocity of an acoustic signal passing through the laminated rock;

determining a composition coefficient based on the acoustic velocities determined, the composition coefficient being indicative of an impact of total organic carbon (TOC) content, rock composition and fluid composition on velocity of an acoustic signal passing through the laminated rock;

generating a rock model for the laminated rock, wherein the rock model comprises:

a velocity component indicative of an acoustic velocity of an acoustic signal passing through the laminated rock;

a stress component comprising a weighting of net stress by the stress coefficient;

a lamination orientation component comprising a weighting of lamination orientation by the lamination orientation coefficient; and a composition component comprising a weighting of TOC, rock composition and fluid composition corresponding to the composition coefficient, the rock model comprising the following:

$$V_p = a_0 + a_1\sigma' + a_2\theta,$$

where:

$$a_0 = b\text{TOC} + \Sigma c_i Vol_{rock\_comp,i} + \Sigma d_i Vol_{fluid\_comp,i},$$

where $V_p$ is acoustic velocity, $a_0$ is the composition coefficient, $a_1$ is the stress coefficient, $a_2$ is the lamination orientation coefficient, $\sigma'$ is a net stress, $\theta$ is lamination orientation, $a_0$ is the composition component, $a_1\sigma'$ is the stress component, $a_2\theta$ is the lamination orientation component, $b$ is a TOC content coefficient, TOC is a value of total organic carbon content, $c_i$ is a rock composition coefficient, $Vol_{rock\_comp,i}$ is a value of rock composition, $d_i$ is a fluid composition coefficient and $Vol_{fluid\_comp,i}$ is a value of fluid composition;

conducting a logging of a wellbore comprising obtaining logging data indicative of an acoustic velocity of acoustic signals passing through second laminated rock of the wellbore in-situ; and determining, based on application of the acoustic velocity of acoustic signals passing through the second laminated rock of the wellbore in-situ to the rock model, a TOC content of the second laminated rock.

8. The method of claim 7, wherein the rock formation comprises a petroleum reservoir, and wherein preparing the plurality of oriented samples of the laminated rock comprises dividing the core sample of the laminated rock extracted from the petroleum reservoir into the plurality of oriented samples of the laminated rock.

9. The method of claim 7, wherein compressing the sample to generate a tri-axial compressive stress on the sample that corresponds to the stress level comprises:
   operating a piston of a test fixture to exert, on the plurality of oriented samples, longitudinal compressive force corresponding to the stress level; and
   pressurizing a substance contained in a radial chamber of the test fixture to exert, on the plurality of oriented samples, lateral compressive force corresponding to the stress level.

10. The method of claim 7, the method further comprising:
   for each lamination orientation, determining a linear expression for the relationship between acoustic velocities and the stress levels for the lamination orientation, the linear expression comprising a slope and a y-intercept associated with the lamination orientation;
   determining a first linear expression for the relationship between the lamination orientations and the corresponding slopes determined, the first linear expression comprising a slopes-slope corresponding to a slope of the first linear expression, and a slopes-intercept corresponding to a y-intercept of the first linear expression;
   determining a second linear expression for the relationship between the lamination orientations and the corresponding y-intercepts determined, the second linear expression comprising an intercepts-slope corresponding to the slope of the second linear expression, and an intercepts-intercept corresponding to a y-intercept of the second linear expression;
   determining the stress coefficient as a value that corresponds to the slopes-intercept;
   determining the lamination orientation coefficient as a value that corresponds to the intercepts-slope; and
   determining the composition coefficient as a value that corresponds to the intercepts-intercept.

11. The method of claim 7, wherein generating a rock model for the laminated rock comprises determining a value for each of the TOC content coefficient, the rock composition coefficient and the fluid composition coefficient based on a value of the composition coefficient.

12. The method of claim 7, the method further comprising controlling, based on the TOC content of the second laminated rock determined, a drilling operation or production operation in a reservoir formation in which the second laminated rock is located.

13. A non-transitory computer readable storage medium comprising program instructions for determining properties of laminated rock, the program instructions executable by a computer processor to cause:
   generate acoustic velocity test data for the laminated rock, the generating comprising:
      for each oriented sample of a plurality of oriented samples of a laminated rock prepared from a core sample of the laminated rock extracted from a rock formation, wherein each of the oriented samples comprises a lamination orientation that is different from lamination orientations of other samples of the plurality of oriented samples:
         for each stress level of a plurality of different stress levels:
            compressing the sample to generate a tri-axial compressive stress on the sample that corresponds to the stress level;
            transmitting a source acoustic pulse through the oriented sample while the oriented sample is subjected to the tri-axial compressive stress, the transmitted pulse being associated with a pulse generation time; and
            sensing a resulting acoustic pulse corresponding to the source acoustic pulse transmitted through the oriented sample while the oriented sample is subjected to the tri-axial compressive stress, the resulting pulse being associated with a pulse receipt time,
            the acoustic velocity test data comprising a subset of acoustic velocity data that is indicative of the pulse generation time and the pulse receipt time, and that is associated with the stress level and the lamination orientation of the oriented sample;
   for each lamination orientation of the lamination orientations of the plurality of oriented samples:
      for each stress level of the plurality of different stress levels:
         determining, based on one or more of the pulse generation times and one or more of the pulse receipt times of the acoustic velocity test data associated with the lamination orientation and the stress level, an acoustic velocity for the lamination orientation and the stress level;
   determining a stress coefficient based on the acoustic velocities determined, the stress coefficient being indicative of an impact of compressive stress on velocity of an acoustic signal passing through the laminated rock;
   determining a lamination orientation coefficient based on the acoustic velocities determined, the lamination orientation coefficient being indicative of an impact of lamination orientation on velocity of an acoustic signal passing through the laminated rock;
   determining a composition coefficient based on the acoustic velocities determined, the composition coefficient being indicative of an impact of total organic carbon (TOC) content, rock composition and fluid composition on velocity of an acoustic signal passing through the laminated rock;
   generating a rock model for the laminated rock, wherein the rock model comprises:
      a velocity component indicative of an acoustic velocity of an acoustic signal passing through the laminated rock;
      a stress component comprising a weighting of net stress by the stress coefficient;
      a lamination orientation component comprising a weighting of lamination orientation by the lamination orientation coefficient; and
      a composition component comprising a weighting of TOC, rock composition and fluid composition corresponding to the composition coefficient,
      the rock model comprising the following:

$$V_p = a_0 + a_1 \sigma' + a_2 \theta,$$

where:

$$a_0 = b\text{TOC} + \Sigma c_i Vol_{rock\_comp,i} + \Sigma d_i Vol_{fluid\_comp,i},$$

where $V_p$ is acoustic velocity, $a_0$ is the composition coefficient, $a_1$ is the stress coefficient, $a_2$ is the lamination orientation coefficient, σ' is a net stress, θ is lamination orientation, $a_0$ is the composition component, $a_1\sigma'$ is the stress component, $a_2\theta$ is the lamination orientation component, b is a TOC content coefficient, TOC is a value of total organic carbon content, $c_i$ is a rock composition coefficient, $Vol_{rock\_comp,i}$ is a value of rock composition, $d_i$ is a fluid composition coefficient and $Vol_{fluid\_comp,i}$ is a value of fluid composition;

conduct a logging of a wellbore comprising obtaining logging data indicative of an acoustic velocity of acoustic signals passing through second laminated rock of the wellbore in-situ; and determining, based on application of the acoustic velocity of acoustic signals passing through the second laminated rock of the wellbore in-situ to the rock model, a TOC content of the second laminated rock.

14. A system for determining properties of laminated rock, comprising:

a laminated rock test system comprising a tri-axial test fixture configured to:
  receive oriented samples of a laminated rock having different lamination orientations, the oriented samples of the laminated rock being prepared from a core sample of the laminated rock extracted from a rock formation; and
  for each of different stress-levels, transmit an acoustic pulse through each of the oriented samples while tri-axially compressing the oriented sample at the stress-level to generate test data indicative of acoustic velocities through the laminated rock at different combinations of lamination orientations and stress levels; and a non-transitory computer readable storage medium comprising program instructions for determining properties of laminated rock, the program instructions executable by a computer processor to cause:
  determining acoustic velocities through the laminated rock at the different combinations of lamination orientations and stress levels based on the test data;
  determining a stress coefficient based on the acoustic velocities determined, the stress coefficient being indicative of an impact of compressive stress on velocity of an acoustic signal passing through the laminated rock;
  determining a lamination orientation coefficient based on the acoustic velocities determined, the lamination orientation coefficient being indicative of an impact of lamination orientation on velocity of an acoustic signal passing through the laminated rock;
  determining a composition coefficient based on the acoustic velocities determined, the composition coefficient being indicative of an impact of total organic carbon (TOC) content, rock composition and fluid composition on velocity of an acoustic signal passing through the laminated rock;
  generating a rock model for the laminated rock based on the acoustic velocities, the rock model comprising the following:

$$V_p = a_0 + a_1\sigma' + a_2\theta,$$

where:

$$a_0 = b\text{TOC} + \Sigma c_i Vol_{rock\_comp,i} + \Sigma d_i Vol_{fluid\_comp,i},$$

where $V_p$ is acoustic velocity, $a_0$ is the composition coefficient, $a_1$ is the stress coefficient, $a_2$ is the lamination orientation coefficient, σ' is a net stress, θ is lamination orientation, $a_0$ is the composition component, $a_1\sigma'$ is the stress component, $a_2\theta$ is the lamination orientation component, b is a TOC content coefficient, TOC is a value of total organic carbon content, $c_i$ is a rock composition coefficient, $Vol_{rock\_comp,i}$ is a value of rock composition, $d_i$ is a fluid composition coefficient and $Vol_{fluid\_comp,i}$ is a value of fluid composition;

conducting a logging of a wellbore comprising obtaining logging data indicative of an acoustic velocity of acoustic signals passing through second laminated rock of the wellbore in-situ; and determining, based on application of the acoustic velocity of acoustic signals passing through the second laminated rock of the wellbore in-situ to the rock model, a property of the second laminated rock.

15. A method for determining properties of laminated rock, the method comprising:

preparing, from a core sample of laminated rock extracted from a rock formation, oriented samples of the laminated rock having different lamination orientations;

for each of different stress-levels, transmit an acoustic pulse through each oriented sample while tri-axially compressing the oriented sample at the stress-level to generate test data indicative of acoustic velocities through the laminated rock at different combinations of lamination orientations and stress levels;

determining acoustic velocities through the laminated rock at the different combinations of lamination orientations and stress levels based on the test data;

determining a stress coefficient based on the acoustic velocities determined, the stress coefficient being indicative of an impact of compressive stress on velocity of an acoustic signal passing through the laminated rock;

determining a lamination orientation coefficient based on the acoustic velocities determined, the lamination orientation coefficient being indicative of an impact of lamination orientation on velocity of an acoustic signal passing through the laminated rock;

determining a composition coefficient based on the acoustic velocities determined, the composition coefficient being indicative of an impact of total organic carbon (TOC) content, rock composition and fluid composition on velocity of an acoustic signal passing through the laminated rock;

generating a rock model for the laminated rock based on the acoustic velocities, the rock model comprising the following:

$$V_p = a_0 + a_1\sigma' + a_2\theta,$$

where:

$$a_0 = b\text{TOC} + \Sigma c_i Vol_{rock\_comp,i} + \Sigma d_i Vol_{fluid\_comp,i},$$

where $V_p$ is acoustic velocity, $a_0$ is the composition coefficient, $a_1$ is the stress coefficient, $a_2$ is the lamination orientation coefficient, σ' is a net stress, θ is lamination orientation, $a_0$ is the composition component, $a_1\sigma'$ is the stress component, $a_2\theta$ is the lamination orientation component, b is a TOC content coefficient, TOC is a value of total organic carbon content, $c_i$ is a rock composition coefficient, $Vol_{rock\_comp,i}$ is a value of rock composition, $d_i$ is a fluid composition coefficient and $Vol_{fluid\_comp,i}$ is a value of fluid composition;

conducting a logging of a wellbore comprising obtaining logging data indicative of an acoustic velocity of acoustic signals passing through second laminated rock of the wellbore in-situ; and determining, based on application of the acoustic velocity of acoustic signals passing through the second laminated rock of the wellbore in-situ to the rock model, a property of the second laminated rock.

16. A non-transitory computer readable storage medium comprising program instructions for determining properties of laminated rock, the program instructions executable by a computer processor to cause:

for each of different stress-levels, transmitting an acoustic pulse through each oriented sample of oriented samples of a laminated rock having different lamination orientations, while tri-axially compressing the oriented sample at the stress-level to generate test data indicative of acoustic velocities through the laminated rock at different combinations of lamination orientations and stress levels, the oriented samples of the laminated rock being prepared from a core sample of the laminated rock extracted from a rock formation;

determining acoustic velocities through the laminated rock at the different combinations of lamination orientations and stress levels based on the test data;

determining a stress coefficient based on the acoustic velocities determined, the stress coefficient being indicative of an impact of compressive stress on velocity of an acoustic signal passing through the laminated rock;

determining a lamination orientation coefficient based on the acoustic velocities determined, the lamination orientation coefficient being indicative of an impact of lamination orientation on velocity of an acoustic signal passing through the laminated rock;

determining a composition coefficient based on the acoustic velocities determined, the composition coefficient being indicative of an impact of total organic carbon (TOC) content, rock composition and fluid composition on velocity of an acoustic signal passing through the laminated rock;

generating a rock model for the laminated rock based on the acoustic velocities, the rock model comprising the following:

$$V_p = a_0 + a_1\sigma' + a_2\theta,$$

where:

$$a_0 = b\text{TOC} + \Sigma c_i Vol_{rock\_comp,i} + \Sigma d_i Vol_{fluid\_comp,i},$$

where $V_p$ is acoustic velocity, $a_0$ is the composition coefficient, $a_1$ is the stress coefficient, $a_2$ is the lamination orientation coefficient, $\sigma'$ is a net stress, $\theta$ is lamination orientation, $a_0$ is the composition component, $a_1\sigma'$ is the stress component, $a_2\theta$ is the lamination orientation component, b is a TOC content coefficient, TOC is a value of total organic carbon content, $c_i$ is a rock composition coefficient, $Vol_{rock\_comp,i}$ is a value of rock composition, $d_i$ is a fluid composition coefficient and $Vol_{fluid\_comp,i}$ is a value of fluid composition;

conducting a logging of a wellbore comprising obtaining logging data indicative of an acoustic velocity of acoustic signals passing through second laminated rock of the wellbore in-situ; and determining, based on application of the acoustic velocity of acoustic signals passing through the second laminated rock of the wellbore in-situ to the rock model, a property of the second laminated rock.

17. A system for determining properties of laminated rock, comprising:

a laminated rock test system configured to generate acoustic velocity test data for a laminated rock, the generating comprising:

receiving a plurality of oriented samples of the laminated rock prepared from a core sample of the laminated rock extracted from a rock formation, wherein each of the oriented samples comprises a lamination orientation that is different from lamination orientations of other samples of the plurality of oriented samples;

for each oriented sample of the plurality of oriented samples:

for each stress level of a plurality of different stress levels:

compress the sample to generate a tri-axial compressive stress on the sample that corresponds to the stress level;

transmit a source acoustic pulse through the oriented sample while the oriented sample is subjected to the tri-axial compressive stress, the transmitted pulse being associated with a pulse generation time; and sense a resulting acoustic pulse corresponding to the source acoustic pulse transmitted through the oriented sample while the oriented sample is subjected to the tri-axial compressive stress, the resulting pulse being associated with a pulse receipt time, the acoustic velocity test data comprising a subset of acoustic velocity data that is indicative of the pulse generation time and the pulse receipt time, and that is associated with the stress level and the lamination orientation of the oriented sample; and a laminated rock assessment module configured to:

for each lamination orientation of the lamination orientations of the plurality of oriented samples:

for each stress level of the plurality of different stress levels:

determine, based on one or more of the pulse generation times and one or more of the pulse receipt times of the acoustic velocity test data associated with the lamination orientation and the stress level, an acoustic velocity for the lamination orientation and the stress level;

determine a stress coefficient based on the acoustic velocities determined, the stress coefficient being indicative of an impact of compressive stress on velocity of an acoustic signal passing through the laminated rock;

determine a lamination orientation coefficient based on the acoustic velocities determined, the lamination orientation coefficient being indicative of an impact of lamination orientation on velocity of an acoustic signal passing through the laminated rock;

determine a composition coefficient based on the acoustic velocities determined, the composition coefficient being indicative of an impact of total organic carbon (TOC) content, rock composition and fluid composition on velocity of an acoustic signal passing through the laminated rock;

for each lamination orientation, determine a linear expression for the relationship between acoustic velocities and the stress levels for the lamination orientation, the linear expression comprising a slope and a y-intercept associated with the lamination orientation;

determine a first linear expression for the relationship between the lamination orientations and the corresponding slopes determined, the first linear expression comprising a slopes-slope corresponding to a slope of the first linear expression, and a slopes-intercept corresponding to a y-intercept of the first linear expression;

determine a second linear expression for the relationship between the lamination orientations and the corresponding y-intercepts determined, the second linear expression comprising an intercepts-slope corresponding to the slope of the second linear expression, and an intercepts-intercept corresponding to a y-intercept of the second linear expression;

determine the stress coefficient as a value that corresponds to the slopes-intercept;

determine the lamination orientation coefficient as a value that corresponds to the intercepts-slope;

determine the composition coefficient as a value that corresponds to the intercepts-intercept;

generate a rock model for the laminated rock, wherein the rock model comprises:
  a velocity component indicative of an acoustic velocity of an acoustic signal passing through the laminated rock;
  a stress component comprising a weighting of net stress by the stress coefficient;
  a lamination orientation component comprising a weighting of lamination orientation by the lamination orientation coefficient; and
  a composition component comprising a weighting of TOC, rock composition and fluid composition corresponding to the composition coefficient;

conduct a logging of a wellbore comprising obtaining logging data indicative of an acoustic velocity of acoustic signals passing through second laminated rock of the wellbore in-situ; and determine, based on application of the acoustic velocity of acoustic signals passing through the second laminated rock of the wellbore in-situ to the rock model, a TOC content of the second laminated rock.

18. The system of claim 17, wherein the rock formation comprises a petroleum reservoir.

19. The system of claim 17, wherein the laminated rock test system comprises a test fixture comprising:
  a piston configured to exert, on the plurality of oriented samples, longitudinal compressive force corresponding to the stress level; and
  a radial chamber configured to contain a pressurized substance configured to exert, on the plurality of oriented samples, lateral compressive force corresponding to the stress level.

20. The system of claim 17, wherein the composition component comprises a value for TOC content weighted by a TOC content coefficient, a value for rock composition weighted by a rock composition coefficient, and a value for fluid composition weighted by a fluid composition coefficient, and wherein generating a rock model for the laminated rock comprises determining a value for each of the TOC content coefficient, the rock composition coefficient and the fluid composition coefficient based on a value of the composition coefficient.

21. The system of claim 17, wherein the rock model comprises the following:

$$V_p = a_0 + a_1 \sigma' + a_2 \theta,$$

where:

$$a_0 = b\text{TOC} + \Sigma c_i Vol_{rock\_comp,i} + \Sigma d_i Vol_{fluid\_comp,i},$$

and where $V_p$ is acoustic velocity, $a_0$ is the composition coefficient, $a_1$ is the stress coefficient, $a_2$ is the lamination orientation coefficient, $\sigma'$ is a net stress, $\theta$ is lamination orientation, $a_0$ is the composition component, $a_1 \sigma'$ is the stress component, $a_2 \theta$ is the lamination orientation component, $b$ is a TOC content coefficient, TOC is a value of total organic carbon content, $c_i$ is a rock composition coefficient, $Vol_{rock\_comp,i}$ is a value of rock composition, $d_i$ is a fluid composition coefficient and $Vol_{fluid\_comp,i}$ is a value of fluid composition.

22. The system of claim 17, wherein the system is configured to control, based on the TOC content of the second laminated rock determined, a drilling operation or production operation in a reservoir formation in which the second laminated rock is located.

23. A method for determining properties of laminated rock, the method comprising:
  preparing a plurality of oriented samples of a laminated rock from a core sample of the laminated rock extracted from a rock formation, wherein each of the oriented samples comprises a lamination orientation that is different from lamination orientations of other samples of the plurality of oriented samples;
  generating acoustic velocity test data for the laminated rock, the generating comprising:
    for each oriented sample of the plurality of oriented samples:
      for each stress level of a plurality of different stress levels:
        compressing the sample to generate a tri-axial compressive stress on the sample that corresponds to the stress level;
        transmitting a source acoustic pulse through the oriented sample while the oriented sample is subjected to the tri-axial compressive stress, the transmitted pulse being associated with a pulse generation time; and
        sensing a resulting acoustic pulse corresponding to the source acoustic pulse transmitted through the oriented sample while the oriented sample is subjected to the tri-axial compressive stress, the resulting pulse being associated with a pulse receipt time,
      the acoustic velocity test data comprising a subset of acoustic velocity data that is indicative of the pulse generation time and the pulse receipt time, and that is associated with the stress level and the lamination orientation of the oriented sample;
  for each lamination orientation of the lamination orientations of the plurality of oriented samples:
    for each stress level of the plurality of different stress levels:
      determining, based on one or more of the pulse generation times and one or more of the pulse receipt times of the acoustic velocity test data associated with the lamination orientation and the stress level, an acoustic velocity for the lamination orientation and the stress level;

determining a stress coefficient based on the acoustic velocities determined, the stress coefficient being indicative of an impact of compressive stress on velocity of an acoustic signal passing through the laminated rock;

determining a lamination orientation coefficient based on the acoustic velocities determined, the lamination orientation coefficient being indicative of an impact of lamination orientation on velocity of an acoustic signal passing through the laminated rock;

determining a composition coefficient based on the acoustic velocities determined, the composition coefficient being indicative of an impact of total organic carbon (TOC) content, rock composition and fluid composition on velocity of an acoustic signal passing through the laminated rock;

for each lamination orientation, determining a linear expression for the relationship between acoustic velocities and the stress levels for the lamination orientation, the linear expression comprising a slope and a y-intercept associated with the lamination orientation;

determining a first linear expression for the relationship between the lamination orientations and the corresponding slopes determined, the first linear expression comprising a slopes-slope corresponding to a slope of the first linear expression, and a slopes-intercept corresponding to a y-intercept of the first linear expression;

determining a second linear expression for the relationship between the lamination orientations and the corresponding y-intercepts determined, the second linear expression comprising an intercepts-slope corresponding to the slope of the second linear expression, and an intercepts-intercept corresponding to a y-intercept of the second linear expression;

determining the stress coefficient as a value that corresponds to the slopes-intercept;

determining the lamination orientation coefficient as a value that corresponds to the intercepts-slope;

determining the composition coefficient as a value that corresponds to the intercepts-intercept;

generating a rock model for the laminated rock, wherein the rock model comprises:
 a velocity component indicative of an acoustic velocity of an acoustic signal passing through the laminated rock;
 a stress component comprising a weighting of net stress by the stress coefficient;
 a lamination orientation component comprising a weighting of lamination orientation by the lamination orientation coefficient; and
 a composition component comprising a weighting of TOC, rock composition and fluid composition corresponding to the composition coefficient;

conducting a logging of a wellbore comprising obtaining logging data indicative of an acoustic velocity of acoustic signals passing through second laminated rock of the wellbore in-situ; and determining, based on application of the acoustic velocity of acoustic signals passing through the second laminated rock of the wellbore in-situ to the rock model, a TOC content of the second laminated rock.

24. The method of claim 23, wherein the rock formation comprises a petroleum reservoir, and wherein preparing the plurality of oriented samples of the laminated rock comprises dividing the core sample of the laminated rock extracted from the petroleum reservoir into the plurality of oriented samples of the laminated rock.

25. The method of claim 23, wherein compressing the sample to generate a tri-axial compressive stress on the sample that corresponds to the stress level comprises:
 operating a piston of a test fixture to exert, on the plurality of oriented samples, longitudinal compressive force corresponding to the stress level; and
 pressurizing a substance contained in a radial chamber of the test fixture to exert, on the plurality of oriented samples, lateral compressive force corresponding to the stress level.

26. The method of claim 23, wherein the composition component comprises a value for TOC content weighted by a TOC content coefficient, a value for rock composition weighted by a rock composition coefficient, and a value for fluid composition weighted by a fluid composition coefficient, and wherein generating a rock model for the laminated rock comprises determining a value for each of the TOC content coefficient, the rock composition coefficient and the fluid composition coefficient based on a value of the composition coefficient.

27. The method of claim 23, wherein the rock model comprises the following:

$$V_p = a_0 + a_1\sigma' + a_2\theta,$$

where:

$$a_0 = b\text{TOC} + \Sigma c_i Vol_{rock\_comp,i} + \Sigma d_i Vol_{fluid\_comp,i},$$

and where $V_p$ is acoustic velocity, $a_0$ is the composition coefficient, $a_1$ is the stress coefficient, $a_2$ is the lamination orientation coefficient, $\sigma'$ is a net stress, $\theta$ is lamination orientation, $a_0$ is the composition component, $a_1\sigma'$ is the stress component, $a_2\theta$ is the lamination orientation component, $b$ is a TOC content coefficient, TOC is a value of total organic carbon content, $c_i$ is a rock composition coefficient, $Vol_{rock\_comp,i}$ is a value of rock composition, $d_i$ is a fluid composition coefficient and $Vol_{fluid\_comp,i}$ is a value of fluid composition.

28. The method of claim 23, the method further comprising controlling, based on the TOC content of the second laminated rock determined, a drilling operation or production operation in a reservoir formation in which the second laminated rock is located.

29. A non-transitory computer readable storage medium comprising program instructions for determining properties of laminated rock, the program instructions executable by a computer processor to cause:
 generate acoustic velocity test data for the laminated rock, the generating comprising:
  for each oriented sample of a plurality of oriented samples of a laminated rock prepared from a core sample of the laminated rock extracted from a rock formation, wherein each of the oriented samples comprises a lamination orientation that is different from lamination orientations of other samples of the plurality of oriented samples:
   for each stress level of a plurality of different stress levels:
    compressing the sample to generate a tri-axial compressive stress on the sample that corresponds to the stress level;
    transmitting a source acoustic pulse through the oriented sample while the oriented sample is subjected to the tri-axial compressive stress, the transmitted pulse being associated with a pulse generation time; and sensing a resulting acoustic pulse corresponding to the source acoustic pulse transmitted through the oriented sample while the oriented sample is subjected to the tri-axial compressive stress, the resulting pulse being associated with a pulse receipt time, the acoustic velocity test data comprising a subset of acoustic velocity data that is indicative of the pulse generation time and the pulse receipt time, and that is associated with the stress level and the lamination orientation of the oriented sample;

for each lamination orientation of the lamination orientations of the plurality of oriented samples:

for each stress level of the plurality of different stress levels:

determining, based on one or more of the pulse generation times and one or more of the pulse receipt times of the acoustic velocity test data associated with the lamination orientation and the stress level, an acoustic velocity for the lamination orientation and the stress level;

determining a stress coefficient based on the acoustic velocities determined, the stress coefficient being indicative of an impact of compressive stress on velocity of an acoustic signal passing through the laminated rock;

determining a lamination orientation coefficient based on the acoustic velocities determined, the lamination orientation coefficient being indicative of an impact of lamination orientation on velocity of an acoustic signal passing through the laminated rock;

determining a composition coefficient based on the acoustic velocities determined, the composition coefficient being indicative of an impact of total organic carbon (TOC) content, rock composition and fluid composition on velocity of an acoustic signal passing through the laminated rock;

for each lamination orientation, determining a linear expression for the relationship between acoustic velocities and the stress levels for the lamination orientation, the linear expression comprising a slope and a y-intercept associated with the lamination orientation;

determining a first linear expression for the relationship between the lamination orientations and the corresponding slopes determined, the first linear expression comprising a slopes-slope corresponding to a slope of the first linear expression, and a slopes-intercept corresponding to a y-intercept of the first linear expression;

determining a second linear expression for the relationship between the lamination orientations and the corresponding y-intercepts determined, the second linear expression comprising an intercepts-slope corresponding to the slope of the second linear expression, and an intercepts-intercept corresponding to a y-intercept of the second linear expression;

determining the stress coefficient as a value that corresponds to the slopes-intercept;

determining the lamination orientation coefficient as a value that corresponds to the intercepts-slope;

determining the composition coefficient as a value that corresponds to the intercepts-intercept;

generating a rock model for the laminated rock, wherein the rock model comprises:

a velocity component indicative of an acoustic velocity of an acoustic signal passing through the laminated rock;

a stress component comprising a weighting of net stress by the stress coefficient;

a lamination orientation component comprising a weighting of lamination orientation by the lamination orientation coefficient; and a composition component comprising a weighting of TOC, rock composition and fluid composition corresponding to the composition coefficient;

conduct a logging of a wellbore comprising obtaining logging data indicative of an acoustic velocity of acoustic signals passing through second laminated rock of the wellbore in-situ; and determining, based on application of the acoustic velocity of acoustic signals passing through the second laminated rock of the wellbore in-situ to the rock model, a TOC content of the second laminated rock.

30. A system for determining properties of laminated rock, comprising:

a laminated rock test system comprising a tri-axial test fixture configured to:

receive oriented samples of a laminated rock having different lamination orientations, the oriented samples of the laminated rock being prepared from a core sample of the laminated rock extracted from a rock formation; and for each of different stress-levels, transmit an acoustic pulse through each of the oriented samples while tri-axially compressing the oriented sample at the stress-level to generate test data indicative of acoustic velocities through the laminated rock at different combinations of lamination orientations and stress levels; and a non-transitory computer readable storage medium comprising program instructions for determining properties of laminated rock, the program instructions executable by a computer processor to cause:

determining acoustic velocities through the laminated rock at the different combinations of lamination orientations and stress levels based on the test data;

determining a stress coefficient based on the acoustic velocities determined, the stress coefficient being indicative of an impact of compressive stress on velocity of an acoustic signal passing through the laminated rock;

determining a lamination orientation coefficient based on the acoustic velocities determined, the lamination orientation coefficient being indicative of an impact of lamination orientation on velocity of an acoustic signal passing through the laminated rock;

determining a composition coefficient based on the acoustic velocities determined, the composition coefficient being indicative of an impact of total organic carbon (TOC) content, rock composition and fluid composition on velocity of an acoustic signal passing through the laminated rock;

for each lamination orientation, determining a linear expression for the relationship between acoustic velocities and the stress levels for the lamination orientation, the linear expression comprising a slope and a y-intercept associated with the lamination orientation;

determining a first linear expression for the relationship between the lamination orientations and the corresponding slopes determined, the first linear expression comprising a slopes-slope corresponding to a slope of the first linear expression, and a slopes-intercept corresponding to a y-intercept of the first linear expression;

determining a second linear expression for the relationship between the lamination orientations and the corresponding y-intercepts determined, the second linear expression comprising an intercepts-slope corresponding to the slope of the second linear expression, and an intercepts-intercept corresponding to a y-intercept of the second linear expression;

determining the stress coefficient as a value that corresponds to the slopes-intercept;

determining the lamination orientation coefficient as a value that corresponds to the intercepts-slope;

determining the composition coefficient as a value that corresponds to the intercepts-intercept;

generating a rock model for the laminated rock based on the acoustic velocities;

conducting a logging of a wellbore comprising obtaining logging data indicative of an acoustic velocity of acoustic signals passing through second laminated rock of the wellbore in-situ; and determining, based on application of the acoustic velocity of acoustic signals passing through the second laminated rock of the wellbore in-situ to the rock model, a property of the second laminated rock.

31. A method for determining properties of laminated rock, the method comprising:

preparing, from a core sample of laminated rock extracted from a rock formation, oriented samples of the laminated rock having different lamination orientations;

for each of different stress-levels, transmit an acoustic pulse through each oriented sample while tri-axially compressing the oriented sample at the stress-level to generate test data indicative of acoustic velocities through the laminated rock at different combinations of lamination orientations and stress levels;

determining acoustic velocities through the laminated rock at the different combinations of lamination orientations and stress levels based on the test data;

determining a stress coefficient based on the acoustic velocities determined, the stress coefficient being indicative of an impact of compressive stress on velocity of an acoustic signal passing through the laminated rock;

determining a lamination orientation coefficient based on the acoustic velocities determined, the lamination orientation coefficient being indicative of an impact of lamination orientation on velocity of an acoustic signal passing through the laminated rock;

determining a composition coefficient based on the acoustic velocities determined, the composition coefficient being indicative of an impact of total organic carbon (TOC) content, rock composition and fluid composition on velocity of an acoustic signal passing through the laminated rock;

for each lamination orientation, determining a linear expression for the relationship between acoustic velocities and the stress levels for the lamination orientation, the linear expression comprising a slope and a y-intercept associated with the lamination orientation;

determining a first linear expression for the relationship between the lamination orientations and the corresponding slopes determined, the first linear expression comprising a slopes-slope corresponding to a slope of the first linear expression, and a slopes-intercept corresponding to a y-intercept of the first linear expression;

determining a second linear expression for the relationship between the lamination orientations and the corresponding y-intercepts determined, the second linear expression comprising an intercepts-slope corresponding to the slope of the second linear expression, and an intercepts-intercept corresponding to a y-intercept of the second linear expression;

determining the stress coefficient as a value that corresponds to the slopes-intercept;

determining the lamination orientation coefficient as a value that corresponds to the intercepts-slope;

determining the composition coefficient as a value that corresponds to the intercepts-intercept;

generating a rock model for the laminated rock based on the acoustic velocities;

conducting a logging of a wellbore comprising obtaining logging data indicative of an acoustic velocity of acoustic signals passing through second laminated rock of the wellbore in-situ; and determining, based on application of the acoustic velocity of acoustic signals passing through the second laminated rock of the wellbore in-situ to the rock model, a property of the second laminated rock.

32. A non-transitory computer readable storage medium comprising program instructions for determining properties of laminated rock, the program instructions executable by a computer processor to cause:

for each of different stress-levels, transmitting an acoustic pulse through each oriented sample of oriented samples of a laminated rock having different lamination orientations, while tri-axially compressing the oriented sample at the stress-level to generate test data indicative of acoustic velocities through the laminated rock at different combinations of lamination orientations and stress levels, the oriented samples of the laminated rock being prepared from a core sample of the laminated rock extracted from a rock formation;

determining acoustic velocities through the laminated rock at the different combinations of lamination orientations and stress levels based on the test data;

determining a stress coefficient based on the acoustic velocities determined, the stress coefficient being indicative of an impact of compressive stress on velocity of an acoustic signal passing through the laminated rock;

determining a lamination orientation coefficient based on the acoustic velocities determined, the lamination orientation coefficient being indicative of an impact of lamination orientation on velocity of an acoustic signal passing through the laminated rock;

determining a composition coefficient based on the acoustic velocities determined, the composition coefficient being indicative of an impact of total organic carbon (TOC) content, rock composition and fluid composition on velocity of an acoustic signal passing through the laminated rock;

for each lamination orientation, determining a linear expression for the relationship between acoustic velocities and the stress levels for the lamination orientation, the linear expression comprising a slope and a y-intercept associated with the lamination orientation;

determining a first linear expression for the relationship between the lamination orientations and the corresponding slopes determined, the first linear expression comprising a slopes-slope corresponding to a slope of the first linear expression, and a slopes-intercept corresponding to a y-intercept of the first linear expression;

determining a second linear expression for the relationship between the lamination orientations and the corresponding y-intercepts determined, the second linear expression comprising an intercepts-slope corresponding to the slope of the second linear expression, and an intercepts-intercept corresponding to a y-intercept of the second linear expression;

determining the stress coefficient as a value that corresponds to the slopes-intercept;

determining the lamination orientation coefficient as a value that corresponds to the intercepts-slope;

determining the composition coefficient as a value that corresponds to the intercepts-intercept;

generating a rock model for the laminated rock based on the acoustic velocities;

conducting a logging of a wellbore comprising obtaining logging data indicative of an acoustic velocity of acoustic signals passing through second laminated rock of the wellbore in-situ; and determining, based on application of the acoustic velocity of acoustic signals passing through the second laminated rock of the wellbore in-situ to the rock model, a property of the second laminated rock.

* * * * *